United States Patent
Schütze et al.

(10) Patent No.: US 6,316,388 B1
(45) Date of Patent: Nov. 13, 2001

(54) N-HETEROARYL-N'-(PYRID-2-YL-SULFONYL) UREAS, PROCESSES FOR THEIR PREPARATION, AND THEIR USE AS HERBICIDES AND PLANT GROWTH REGULATORS

(75) Inventors: Rainer Schütze, Idstein/Taunus; Heinz Kehne, Hofheim am Taunus; Klaus Bauer, Hanau; Hermann Bieringer, Eppstein/Taunus, all of (DE)

(73) Assignee: Hoechst Schering AgrEvo GmbH, Frankfurt am Main (DE)

( * ) Notice: Subject to any disclaimer, the term of this patent is extended or adjusted under 35 U.S.C. 154(b) by 0 days.

(21) Appl. No.: 08/333,882

(22) Filed: Nov. 3, 1994

Related U.S. Application Data

(63) Continuation of application No. 08/016,758, filed on Feb. 11, 1993.

(30) Foreign Application Priority Data

Feb. 14, 1992 (DE) .................................. 42 04 411

(51) Int. Cl.[7] .................. A01N 47/36; C07D 491/00; C07D 239/02
(52) U.S. Cl. .................. 504/215; 504/210; 544/253; 544/278; 544/319; 544/320
(58) Field of Search .................. 544/253, 278, 544/319, 320; 504/215, 210

(56) References Cited

U.S. PATENT DOCUMENTS

| | | |
|---|---|---|
| 4,421,550 | 12/1983 | Selby et al. . |
| 4,487,626 | 12/1984 | Zimmermann . |
| 4,579,583 | 4/1986 | Föry et al. . |
| 5,125,956 | * 6/1992 | Korte ..................... 546/193 |
| 5,221,316 | * 6/1993 | Anthony ................ 546/193 |
| 5,296,453 | * 3/1994 | Le-Si ..................... 544/320 |

FOREIGN PATENT DOCUMENTS

| | | |
|---|---|---|
| 78046/91 | 12/1991 | (AU) . |
| 0013480 | 7/1980 | (EP) . |
| 0084224 | 7/1983 | (EP) . |
| 0103543 | 3/1984 | (EP) . |
| 0125864 | 11/1984 | (EP) . |
| 0237292 | 9/1987 | (EP) . |
| 0272855 | 6/1988 | (EP) . |
| 0451468 | 10/1991 | (EP) . |
| 0459949 | 12/1991 | (EP) . |
| WO 88/04297 | 6/1988 | (WO) . |
| WO 91/10660 | 7/1991 | (WO) . |
| 91/0173 | 1/1991 | (ZA) . |

OTHER PUBLICATIONS

Chemical Abstracts 108: 21919v, Kimura et al, Abstract of EP 232067, Published Aug. 1987.*
CA 108: 21919v by Kimura et al. Abstract of EP232067 Published Aug. 1987.*
Chemical Abstracts 108: 21919v by Kimura et al, Abstract of EP 232067, Published Aug. 1987.*
Chemical Abstract, vol. 118, No. 15, Apr. 12, 1992, p. 844.

* cited by examiner

Primary Examiner—D. Margaret Seaman
(74) Attorney, Agent, or Firm—Frommer Lawrence & Haug LLP

(57) ABSTRACT

N-Heteroaryl-N'-(pyrid-2-yl-sulfonyl)ureas, processes for their preparation, and their use as herbicides and plant growth regulators Compounds of the formula (I)

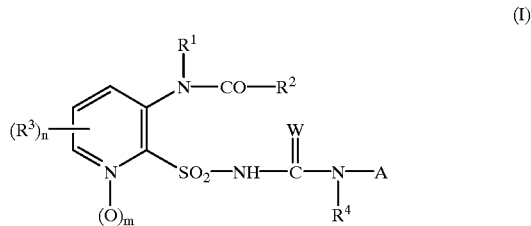

in which
$R^1$—$R^4$, A, n, m and w are as defined in claim 1, are suitable as herbicides for controlling harmful plants and can be prepared, inter alia, from the sulfonamides of the formula (II)

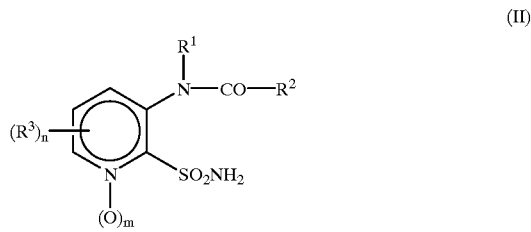

by reacting them with carbamates R*O—CO—$NR^4$—A.

46 Claims, No Drawings

N-HETEROARYL-N'-(PYRID-2-YL-SULFONYL) UREAS, PROCESSES FOR THEIR PREPARATION, AND THEIR USE AS HERBICIDES AND PLANT GROWTH REGULATORS

This application is a continuation of application Ser. No. 08/016,758, filed Feb. 11, 1993.

The invention relates to the technical field of herbicides and plant growth regulators, in particular herbicides for the selective control of dicotyledon weeds and grass weeds in crops of useful plants.

It is known that some 2-pyridylsulfonylureas have herbicidal and plant-growth-regulating properties; compare EP-A-13,480, EP-A-272,855, EP-A-84,224, U.S. Pat. No. 4,421,550, EP-A-103,543 (U.S. Pat. No. 4,579,583) U.S. Pat. No. 4,487,626, EP-A-125,864, WO 88/04,297 and WO 91/10,660 (ZA 91/0,173).

More 2-pyridylsulfonylureas which have specific radicals in the 3-position of the pyridyl radical and which are suitable as herbicides and plant growth regulators have now been found.

The present invention relates to compounds of the formula (I) or salts thereof

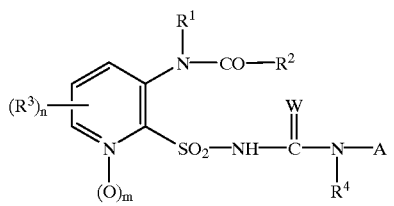

(I)

in which
R$^1$ is H, (C$_1$–C$_6$)alkyl which is unsubstituted or substituted by one or more radicals selected from the group comprising halogen, nitro, (C$_1$–C$_4$)alkoxy, (C$_3$–C$_6$)cycloalkyl, aryl and substituted aryl, or aryl in which the aryl radical is unsubstituted or substituted by one or more radicals selected from the group comprising halogen, nitro, (C$_1$–C$_4$)alkyl, (C$_1$–C$_4$)haloalkyl and (C$_1$–C$_4$)alkoxy, R$^2$ is H, (C$_1$–C$_6$)alkyl, (C$_2$–C$_6$)alkenyl or (C$_2$–C$_6$)alkynyl, each of the three last-mentioned radicals being unsubstituted or substituted by one or more radicals selected from the group comprising halogen, (C$_1$–C$_4$)alkoxy, (C$_1$–C$_4$)alkylthio, (C$_1$–C$_4$)alkylsulfynyl, (C$_1$–C$_4$)alkylsulfonyl, nitro, cyano and thiocyanato, or (C$_1$–C$_6$)alkoxy or (C$_1$–C$_6$)alkylthio, the last-mentioned 2 radicals being unsubstituted or substituted by one or more radicals selected from the group comprising halogen, (C$_1$–C$_4$)alkoxy, (C$_1$–C$_4$)alkylthio, aryl and substituted aryl, (C$_3$–C$_7$)cycloalkyl or (C$_3$–C$_7$)cycloalkoxy, the last-mentioned 2 radicals being unsubstituted or substituted by one or more radicals selected from the group comprising (C$_1$–C$_4$)alkyl, (C$_1$–C$_4$)alkoxy, (C$_1$–C$_4$)alkylthio, (C$_1$–C$_4$)haloalkyl and halogen, or aryl, substituted aryl or a radical of the formula NR$^a$R$^b$, R$^3$ is (C$_1$–C$_4$)alkyl, (C$_1$–C$_3$)haloalkyl, halogen, NO$_2$, CN, (C$_1$–C$_3$) or (C$_1$–C$_4$)-alkoxy, (C$_1$–C$_3$) haloalkoxy, (C$_1$–C$_3$)alkylthio, (C$_1$–C$_3$)alkoxy-(C$_1$–C$_3$)alkyl, [(C$_1$–C$_3$)alkoxy]-carbonyl, (C$_1$–C$_3$)alkylamino, di[(C$_1$–C$_3$)alkyl]-amino, (C$_1$–C$_6$)-alkylsulfynyl, (C$_1$–C$_3$)alkylsulfonyl, SO$_2$NR$^c$R$^d$ or C(O)NR$^e$R$^f$, R$^a$, R$^b$, R$^c$, R$^d$, R$^e$ and R$^f$ independently of one another are H, (C$_1$–C$_4$)alkyl, (C$_3$–C$_6$)alkenyl, (C$_3$–C$_6$)alkynyl, [(C$_1$–C$_4$)alkyl]-carbonyl, arylcarbonyl, which is unsubstituted or substituted in the aryl radical, or the pairs R$^a$ and R$^b$, R$^c$ and R$^d$ or R$^e$ and R$^f$ together with the N atom linking them are a heterocyclic saturated or unsaturated ring which is unsubstituted or substituted and which has 3 to 7 ring atoms and 0, 1 or 2 further hetero atoms selected from the group comprising N, O and S, R$^4$ is H or (C$_1$–C$_4$)alkyl, preferably H or CH$_3$, in particular H, m is 0 or 1, preferably 0, n is 0, 1 or 2, preferably 0 or 1, A is a radical of the formula

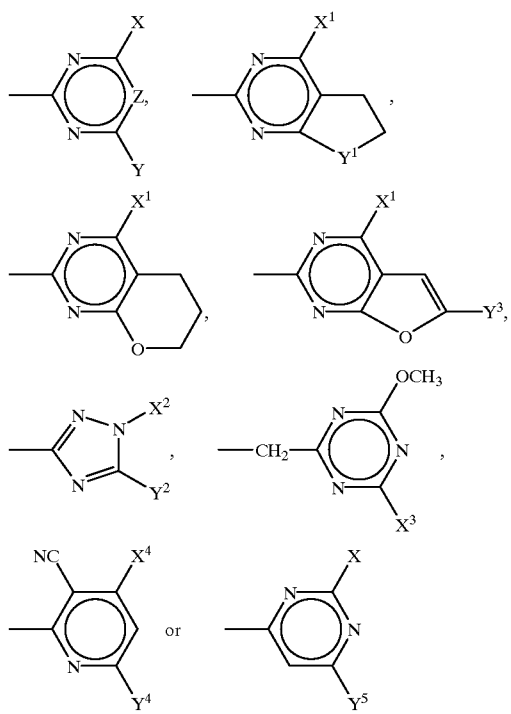

X and Y independently of one another are H, halogen, (C$_1$–C$_3$)alkyl, (C$_1$–C$_3$)alkoxy or (C$_1$–C$_3$)alkylthio, the abovementioned alkyl-containing radicals being unsubstituted or mono- or polysubstituted by halogen or mono- or disubstituted by (C$_1$–C$_3$)alkoxy or (C$_1$–C$_3$) alkylthio, or a radical of the formula NR$^5$R$^6$, (C$_3$–C$_6$) cycloalkyl, (C$_2$–C$_4$)alkenyl, (C$_2$–C$_4$)alkynyl, (C$_3$–C$_4$) alkenyloxy or (C$_3$–C$_4$)alkynyloxy, R$^5$ and R$^6$ independently of one another are H, (C$_1$–C$_3$) alkyl or (C$_3$–C$_4$)alkenyl, W is O or S, preferably O, Z is CH or N, preferably CH, X$^1$ is CH$_3$, OCH$_3$, OC$_2$H$_5$ or OCF$_2$H, Y$^1$ is —O— or —CH$_2$—, X$^2$ is CH$_3$, C$_2$H$_5$ or CH$_2$CF$_3$, Y$^2$ is OCH$_3$, OC$_2$H$_5$, SCH$_3$, SC$_2$H$_5$, CH$_3$ or C$_2$H$_5$, X$^3$ is CH$_3$ or OCH$_3$, Y$^3$ is H or CH$_3$, X$^4$ is CH$_3$, OCH$_3$, OC$_2$H$_5$, CH$_2$OCH$_3$ or Cl, Y$^4$ is CH$_{31}$ OCH$_3$, OC$_2$H$_5$ or Cl, Y$^5$ is CH$_3$, C$_2$H$_5$, OCH$_3$ or Cl.

In formula (I) and hereinafter, hydrocarbon-containing radicals such as, for example, alkyl, alkoxy, haloalkyl and alkylthio radicals as well as the corresponding unsaturated and/or substituted radicals can in each case be straight-chain or branched in the hydrocarbon moiety. Alkyl radicals, also in composite meanings such as alkoxy, haloalkyl and the like, are methyl, ethyl, n- or i-propyl or n-, i-, t- or 2-butyl; alkenyl and alkynyl radicals have the meanings of the unsaturated radicals which are possible and which correspond to the alkyl radicals, such as 2-propenyl, 2- or 3-butenyl, 2-propynyl or 2- or 3-butynyl. Halogen is fluorine, chlorine, bromine or iodine. Haloalkyl is alkyl which is substituted by one or more atoms selected from the group comprising halogen; haloalkyl is, for example, $CF_3$, $CHF_2$, $CH_2CF_3$. Aryl is, for example, phenyl, naphthyl, tetrahydronaphthyl, indanyl, fluorenyl and the like, preferably phenyl. Substituted aryl or substituted phenyl is preferably aryl or phenyl each of which is substituted by one or more, preferably 1 to 3, radicals selected from the group comprising halogen, alkyl, haloalkyl, haloalkoxy, nitro, cyano, alkoxycarbonyl, alkanoyl, carbamoyl, mono- and dialkylaminocarbonyl, mono- and dialkylamino, alkylsulfynyl or alkylsulfonyl, preferred alkyl-containing radicals being those which have 1 to 4 carbon atoms, in particular 1 to 2 carbon atoms; particularly preferred are methyl, methoxy and chlorine. Examples of heterocyclic radicals $R^2=NR^aR^b$ are pyrrole, imidazole, pyrazole, triazole, pyrazolone, oxazoles, oxazolones, propane sultams, butane sultams, pyrrolidone, piperidine and morpholine.

The invention also relates to all stereoisomers which are embraced by formula (I) and mixtures thereof. Such compounds of the formula (I) contain one or more asymmetric carbon atoms or else double bonds which are not mentioned separately in the formulae (I). The possible stereoisomers which are defined by their specific spatial arrangement such as enantiomers, diastereomers, Z and E isomers, however, are all embraced by formulae I and can be obtained from mixtures of the stereoisomers by customary methods or else by stereoselective reactions in combination with the use of stereochemically pure starting materials.

The compounds of the formula (I) can form salts in which the hydrogen of the —$SO_2$—NH—group is replaced by an agriculturally suitable cation. Examples of these salts are metal salts, in particular alkali metal or alkaline earth metal salts, or else ammonium salts or salts with organic amines. Salt formation can equally be effected by addition reaction with a strong acid with the pyridine moiety of the compound of the formula (I). Acids which are suitable for this purpose are strong inorganic and organic acids, for example HCl, HBr, $H_2SO_4$ or $HNO_3$.

Preferred compounds of the formula I according to the invention or salts thereof are those in which $R^1$ is H, $(C_1-C_4)$alkyl which is unsubstituted or substituted by 1 to 3 radicals selected from the group comprising halogen or by $(C_1-C_2)$alkoxy or $(C_3-C_5)$cycloalkyl.

Other preferred compounds of the formula (I) according to the invention or salts thereof are those in which $R^2$ is H, $(C_1-C_4)$alkyl which is unsubstituted or substituted by one or more halogen atoms or by $(C_1-C_2)$alkoxy, or $(C_2-C_4)$alkenyl, $(C_2-C_3)$alkynyl, $(C_3-C_5)$cycloalkyl, $(C_1-C_4)$alkoxy which is unsubstituted or substituted by one or more halogen atoms or by phenyl, or a radical of the formula $NR^aR^b$ in which $R^a$ and $R^b$ independently of one another are H or $(C_1-C_4)$alkyl.

Other preferred compounds of the formula (I) according to the invention or salts thereof are those in which $R^3$ is $(C_1-C_4)$alkyl, $(C_1-C_3)$haloalkyl, halogen, $(C_1-C_3)$alkoxy or nitro and n is 0, 1 or 2, preferably 0 or 1.

Other preferred compounds of the formula (I) or salts thereof are those in which $R^1$ is H, $(C_1-C_4)$alkyl, $(C_1-C_4)$haloalkyl or $[(C_1-C_2)$alkoxy]-$(C_1-C_2)$alkyl, $R^2$ is H, $(C_1-C_4)$alkyl, halo-$(C_1-C_4)$alkyl, $(C_2-C_4)$alkenyl, $(C_2-C_4)$alkynyl, $(C_1-C_4)$alkoxy, $[(C_1-C_2)$alkoxy]-$(C_1-C_2)$alkyl, $(C_3-C_5)$cycloalkyl or a radical of the formula $NR^aR^b$ in which $R^a$ and $R^b$ independently of one another are H or $(C_1-C_4)$alkyl, $R^3$ is $(C_1-C_4)$alkyl, halogen, nitro or $(C_1-C_4)$alkoxy and n is 0 or 1.

Other preferred compounds according to the invention are those in which $R^1$ is H, $CH_3$ or $C_2H$ and $R^2$ is H, $(C_1-C_4)$alkyl, $(C_1-C_2)$haloalkyl, vinyl, cyclopropyl, cyclobutyl, $(C_1-C_2)$alkoxy or $N(CH_3)_2$, in particular H.

Other preferred compounds of the formula (I) or salts thereof are those in which A is a radical of the formula

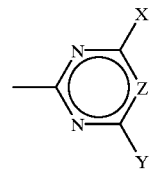

It is preferred for one of the radicals X and Y to be $(C_1-C_3)$alkyl, $(C_1-C_3)$alkoxy, $(C_1-C_3)$haloalkyl, $(C_1-C_3)$haloalkoxy or $[(C_1-C_2)$alkoxy]-$(C_1-C_2)$alkyl and for the other radical Y or X to be $(C_1-C_3)$alkyl, $(C_1-C_3)$alkoxy or $(C_1-C_3)$alkylthio, each of the last-mentioned 3 radicals being unsubstituted or mono- or polysubstituted by halogen or mono- or disubstituted by $(C_1-C_3)$alkoxy or $(C_1-C_3)$alkylthio, or halogen or a radical of the formula $NR^5R^6$ in which $R^5$ and $R^6$ independently of one another are H, $(C_1-C_3)$alkyl or $(C_3-C_4)$alkenyl, or $(C_3-C_6)$cycloalkyl, $(C_2-C_4)$alkenyl, $(C_2-C_4)$alkynyl, $(C_3-C_4)$alkenyloxy or $(C_3-C_4)$alkynyloxy.

It is even more preferred for one of the radicals X and Y to be $(C_1-C_2)$alkyl, $(C_1-C_2)$alkoxy or $OCF_2H$ and for the other radical Y or X to be $(C_1-C_2)$alkyl, $(C_1-C_2)$alkoxy, halogen, $OCF_2H$, $OCH_2CF_3$ or $CF_3$.

In particular, X and Y independently of one another are $(C_1-C_2)$alkyl or $(C_1-C_2)$alkoxy.

Other preferred compounds of the formula (I) according to the invention or salts thereof are those in which there is a combination of two or more of the meanings (features) mentioned as being preferred.

The present invention furthermore relates to processes for the preparation of the compounds of the formula (I) according to the invention or salts thereof, which comprise a) reacting a compound of the formula (II)

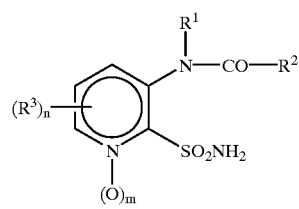

(II)

with a heterocyclic carbamate of the formula (III)

R*—O—CO—$NR^4$—A   (III)

in which R* is optionally substituted phenyl or $(C_1-C_4)$alkyl, or b) reacting a pyridylsulfonylcarbamate of the formula (IV)

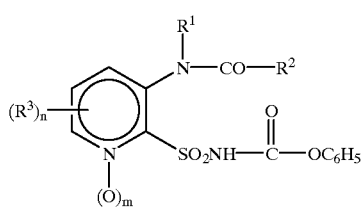
(IV)

with an amino heterocycle of the formula (V)

(V)

or c) reacting a sulfonyl isocyanate of the formula (VI)

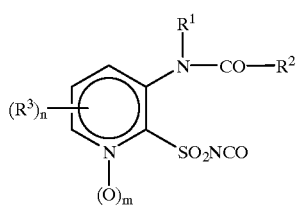
(VI)

with an amino heterocycle of the formula (V)

(V)

or d) reacting, in a one-pot reaction, first an amino heterocycle of the formula H—NR$^4$—A (V) with phosgene in the presence of a base such as, for example, triethylamine, and reacting the intermediate formed with a pyridinesulfonamide of the formula (II), where, in formulae (II)–(VI), R$^1$, R$^2$, R$^3$, R$^4$, A, m and n are as defined in formula I.

The reaction of the compounds of the formulae (II) and (III) is preferably carried out with base catalysis in an inert organic solvent such as, for example, dichloromethane, acetonitrile, dioxane or THF, at temperatures between 0° C. and the boiling point of the solvent. Bases which are used are, for example, 1,8-diazabicyclo[5.4.0]undec-7-ene (DBU) or trimethylaluminum or triethylaluminum.

The sulfonamides (II) are novel compounds. They and their preparation also form part of the invention.

The compound of the formula (II) is obtained for example starting from compounds of the formula (VII)

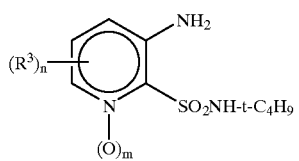
(VII)

by reacting them with carboxylic acid halides of the formula Hal—CO—R$^2$ (Hal=halogen, preferably chlorine) or symmetric or mixed carboxylic anhydrides of the formula R$^2$—CO—O—CO—R$^+$, in which R$^+$ is defined analogously to R$^2$ or is another aliphatic or aromatic radical, followed by reaction of the resulting 3-(N-acylamino)pyridine2-sulfamide which is protected with the t-butyl group a) with a strong acid (for example trifluoroacetic acid) to give the free 3-(N-acylamino)pyridine2-sulfamide of the formula (II) in which R$^1$=H, or b) by reduction, for example with lithium aluminum hydride (reduction of the acyl group to give the optionally substituted N-alkyl group) followed by second N-acylation with a compound of the formula Hal—CO—R$^2$ or R$^2$—CO—O—CO—R and elimination of the t-butyl protective group with a strong acid (for example trifluoroacetic acid) to give the free 3-(N-acylamino)pyridine-2-sulfamide of the formula II, in which R$^1$ is other than hydrogen.

The individual reaction steps can be carried out analogously to conventional processes. The sulfonamides of the formula (VII) can be prepared by processes known from the literature from 2-chloro-3-nitropyridine, or 2-chloro3-aminopyridine, by reaction with sulfur nucleophiles such as, for example, benzylmercaptan, if appropriate reduction of the nitro group, followed by oxidative chlorination of the sulfur atom using sodium hypochlorite or chlorine (formation of the sulfonyl chlorides analogously to EP-A-272,855) and reaction of the sulfonyl chlorides obtained with tert.-butylamine.

A further derivatization step can be carried out at the level of the sulfonamides which are protected by the tert.-butyl groups, for example by nucleophilic substitution with S-alkyl compounds.

Alternatively, compounds of the formula (II) can be prepared from 2-chloro-3-aminopyridine by N-acylation and N-alkylation, formation of the sulfonyl chlorides as described above and reaction of the sulfonyl chlorides directly with ammonia, by or analogously to conventional methods.

The carbamates of the formula (III) can be prepared by methods which are described in South AFrican Patent Applications 82/5671 and 82/5045 or EP-A-70,804 (U.S. Pat. No. 4,480,101) or Research Disclosure RD 275056.

The reaction of the compounds (IV) with the amino heterocycles (V) is preferably carried out in inert, aprotic solvents such as, for example, dioxane, acetonitrile or tetrahydrofuran, at temperatures between 0° C. and the boiling point of the solvent. The pyridylsulfonylcarbamates of the formula (IV) are obtained analogously to EP-A-44,808 or EP-A-237,292.

The pyridylsulfonyl isocyanates of the formula (VI) can be prepared analogously to EP-A-184,385 and reacted with the amino heterocycles of the formula (V).

The salts of the compounds of the formula (I) are preferably prepared in inert solvents such as, for example, water, methanol or acetone, at temperatures from 0 to 100° C. Bases which are suitable for the preparation of salts according to the invention are, for example, alkali metal carbonates such as potassium carbonate, alkali metal hydroxides and alkaline earth metal hydroxides, ammonia or ethanolamine. Acids which are particularly suitable for salt formation are HCl, HBr, H$_2$SO, or HNO$_3$.

The "inert solvents" referred to in the above process variants are to be understood as meaning in each case solvents which are inert under the reaction conditions in question but which need not be inert under any desired reaction condition.

The compounds of the formula (I) according to the invention or salts thereof have an excellent herbicidal activity against a broad range of economically important monocotyledon and dicotyledon harmful plants. The active substances also act efficiently on perennial weeds which produce shoots from rhizomes, rootstocks or other perennial organs and which are difficult to control. In this context, it does not matter whether the substances are applied before sowing, pre-emergence or post-emergence. Specifically, examples may be mentioned of some representatives of the monocotyledon and dicotyledon weed flora which can be controlled by the compounds according to the invention, without the enumeration being a restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledon weed species, the range of action extends to species such as, for example, Galium, viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active substances according to the invention equally effect outstanding control of weeds which occur under the specific conditions of rice growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence on the green parts of the plants, growth likewise stops drastically a very short time after the treatment and the weed plants remain at the growth stage at the point of time of application, or they die completely after a certain time, so that in this manner competition by the weeds, which is harmful to the crop plants, is eliminated at a very early point in time and in a sustained manner.

Even though the compounds according to the invention have an excellent herbicidal activity against monocotyledon and dicotyledon weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling undesired plant growth in plantings for agricultural use.

In addition, the compounds of the formula (I) according to the invention have excellent growth-regulating properties in crop plants. They engage in the plant metabolism in a regulating manner and can thus be employed for the targeted control of plant constituents and for facilitating harvesting, such as, for example, by provoking desiccation and stunted growth. Furthermore, they are also suitable for generally regulating and inhibiting undesired vegetative growth, without simultaneously destroying the plants. Inhibition of vegetative growth plays an important role in many monocotyledon and dicotyledon crops because lodging can be reduced hereby, or prevented completely.

The compounds of the formula (I) according to the invention can be employed in the conventional preparations in the form of wettable powders, emulsifiable concentrates, sprayable solutions, dusts or granules. The invention therefore also relates to herbicidal and plant-growth-regulating compositions which comprise compounds of the formula (I) or salts thereof.

The compounds of the formula (I) or salts thereof can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing agents, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations" Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schdönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Based on these formulations, it is also possible to prepare combinations with other pesticidally active substances, such as insecticides, acaricides, herbicides, fungicides, safeners, fertilizers and/or growth regulators, for example in the form of a ready-mix or a tank mix.

Wettable powders are preparations which are uniformly dispersible in water and which, besides the active substance, also contain ionic or nonionic surfactants (wetting agents, dispersants), for example, polyoxyethylated alkylphenols, polyoxethylated fatty alcohols and polyoxethylated fatty amines, fatty alcohol polyglycol ether sulfates, alkanesulfonates, alkylbenzenesulfonates, sodium ligninsulfonate, sodium 2,2'-dinaphthylmethane-6,6'-disulfonate, sodium dibutylnaphthalene sulfonate or else sodium oleoylmethyltaurate, in addition to a diluent or inert substance.

To prepare the wettable powders, the herbicidal active substances are ground finely, for example in conventional apparatus such as swing-hammer crushers, blowing mills and air-jet mills, and mixed with the formulation auxiliaries, either simultaneously or subsequently.

Emulsifiable concentrates can be prepared by dissolving the active substance in an organic solvent, for example butanol, cyclohexanone, dimethylformamide, xylene and also higher-boiling aromatics or hydrocarbons, or mixtures of the organic solvents, with the addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan, esters such as, for example, sorbitan fatty acid esters or polyoxyethylene sorbitan esters such as, for example, polyoxyethylene sorbitan fatty acid esters.

Dusts are obtained by grinding the active substance with finely divided solid substances, for example talc or natural clays, such as kaolin, bentonite and pyrophyllite, or diatomaceous earth.

Suspension concentrates can be water- or oil-based. They can be prepared for example by wet grinding, by means of commercially available bead mills and, if appropriate, with addition of surfactants, as have already been mentioned, for example, above in the case of other formulation types.

Emulsions, for example oil-in-water emulsions (EW), can be prepared, for example, by means of stirrers, colloid mills and/or static mixers using aqueous organic solvents and, if appropriate, surfactants, as have already been mentioned, for example, above in the case of the other formulation types.

Granules can be produced either by spraying the active substance onto adsorptive, granulated inert material or by applying active substance concentrates onto the surface of carriers such as sand, kaolinites or of granulated inert material, by means of binders, for example polyvinyl alcohol, sodium polyacrylate or else mineral oils. Suitable active substances can also be granulated in the manner which is conventional for the production of fertilizer granules, if desired in a mixture with fertilizers.

Water-dispersible granules are generally prepared by conventional processes such as spray-drying, fluidized-bed granulation, disk granulation, mixing with high-speed mixers and extrusion without solid inert material.

The agrochemical preparations generally comprise 0.1 to 99% by weight, in particular 0.1 to 95% by weight, of active substance of the formula (I) or salts thereof.

The active substance concentration in wettable powders is, for example, about 10 to 90% by weight; the remainder to 100% by weight is composed of conventional formulation components. In the case of emulsifiable concentrates, the active substance concentration can be about 1 to 90, preferably 5 to 80, % by weight. Formulations in the form of dusts contain 1 to 30, preferably mostly 5 to 20, % by weight of active substance, sprayable solutions about 0.05 to 80, preferably 2 to 50, % by weight of active substance. In the case of water-dispersible granules, the active substance content depends partly on whether the active compound is liquid or solid and on which granulation auxiliaries, fillers etc. are used. The active substance content is, for example, between 1 and 95% by weight, preferably between 10 and 80% by weight in the case of the water-dispersible granules.

In addition, the active substance formulations mentioned comprise, if appropriate, the adhesives, wetting agents, dispersing agents, emulsifiers, penetrants, preservatives, antifreeze agents, solvents, fillers, carriers, colorants, defoamers, evaporation inhibitors and pH and viscosity regulators which are conventional in each case.

Components which can be combined with the active substances according to the invention in mixed formulations or in a tank mix are, for example, known active substances as are described, for example, in Weed Research 26, 441–445 (1986), or "The Pesticide Manual", 9th edition, The British Crop Protection Council, 1990/91, Bracknell, England, and the literature cited therein. Herbicides which are known from the literature which can be combined with the compounds of the formula (I) are, for example, the following active substances (note: the compounds are either designated by the "common name" as given by the International Organization for Standardization (ISO) or by the chemical name, if appropriate together with a conventional code number): acetochlor; acifluorfen; aclonifen; AKH 7088, i.e. [[[1-[5-[2-chloro-4-(trifluoromethyl)-phenoxy]-2-nitrophenyl]-2-methoxyethylidene]-amino]-oxy]acetic acid and -acetic acid methyl ester; alachlor; alloxydim; ametryn; amidosulfuron; amitrole; AMS, i.e. ammonium sulfamate; anilofos; asulam; atrazine; aziprotryne; barban; BAS 516 H, i.e. 5-fluoro-2-phenyl-4H-3,1-benzoxazin-4-one; benazolin; benfluralin; benfuresate; bensulfuronmethyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; carbetamide; CDAA, i.e. 2-chloro-N,N-di2-propenylacetamide; CDEC, i.e. 2-chloroallyl diethyldithiocarbamate; CGA 184927, i.e. 2-[4-[(5-chloro3-fluoro-2-pyridinyl)oxy]phenoxy]propanoic acid and 2-propynyl ester; chlomethoxyfen; chloramben; chlorazifop-butyl, pirifenop-butyl; chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamide; cinmethylin; cinosulfuron; clethodim; clomazone; clomeprop; cloproxydim; clopyralid; cyanazine; cycloate; cycloxydim; cycluron; cyperquat; cyprazine; cyprazole; 2,4-DB; dalapon; desmediphan; desmetryn; di-allate; dicamba; dichlobenil; dichlorprop; diclofop-methyl; diethatyl; difenoxuron; difenzoquat; diflufenican; dimefuron; dimethachlor; dimethametryn; dimethazone, clomazon; dimethipin; dimetrasulfuron, cinosulfuron; dinitramine; dinoseb; dinoterb; diphenamid; dipropetryne; diquat; dithiopyr; diuron; DNOC; eglinazine-ethyl; EL 177, i.e. 5-cyano-1-(1,1-dimethylethyl)-N-methyl-3H-pyrazole-4-carboxamide; endothal; EPTC; esprocarb; ethalfluralin; ethametsulfuronmethyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; F6285, i.e. 1-[5-(N-methylsulfonyl)-amino-2,4-dichlorophenyl]-3-methyl-4-difluoromethyl-1,2,4-triazol-5-one; fenoprop; fenoxan, s. clomazone; fenoxaprop-ethyl; fenuron; flamprop-methyl; flazasulfuron; fluazifop and its ester derivatives; fluchloralin; flumetsulam; N-[2,6-difluorophenyl]-5-methyl-(1,2,4)-triazolo[1,5a]pyrimidin-2-sulfonamide; flumeturon; flumipropyne; fluorodifen; fluoroglycofen-ethyl; fluridone; flurochloridone; fluroxypyr; flurtamone; fomesafen; fosamine; furyloxyfen; glufosinate; glyphosate; halosaten; haloxyfop and its ester derivatives; hexazinone; Hw 52, i.e. N-(2,3-dichlorophenyl)-4-(ethoxymethoxy)-benzamide; imazamethabenz-methyl; imazapyr; imazaquin; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidide; metamitron; metazachlor; methabenzthiazuron; metham; methazole; methoxyphenone; methyldymron; metobromuron; metolachlor; metoxuron; metribuzin; metsulfuron-methyl; MH; molinate; monalide; monocarbamide dihydrogensulfate; monolinuron; monuron; MT 128, i.e. 6-chloro-N-[3-chloro-2-propenyl)-5-methyl-N-phenyl-3-pyridazinamine; MT 5950, i.e. N-t-3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiazon; oxyfluorfen; paraquat; pebulate; pendimethalin; perfluidone; phenmedipham; phenisopham; phenmedipham; picloram; piperophos; piributicarb; pirifenop-butyl; pretilachlor; primisulfuron-methyl; procyazine; prodiamine; profluralin;

proglinazine-ethyl; prometon; prometryn; propachlor; propanil; propaquizafop and its ester derivatives; propazine; propham; propyzamide; prosulfalin; prosulfocarb; prynachlor; pyrazolinate; pyrazon; pyrazosulfuron-ethyl; pyrazoxyfen; pyridate; quinclorac; quinmerac; quinofop and its ester derivatives, quizalofop and its ester derivatives; quizalofop-ethyl; quizalofop-p-tefuryl; renriduron; dymron; S 275, i.e. 2-[4-chloro-2-fluoro-5-(2-propynyl-oxy)-phenyl]-4,5,6,7-tetrahydro-2H-indazole; S 482, i.e. 2-[7-fluoro-3,4-dihydro-3-oxo-4-(2-propynyl)-2H-1,4-benzoxazin-6-yl]-4,5,6,7-tetrahydro-1H-isoindole -1,3(2H)-dione; secbumeton; sethoxydim; siduron; simazine; simetryn; SN 106279, i.e. 2-[[7-[2-chloro-4-(trifluoromethyl)-phenoxy]-2-naphthalenyl]-oxy]-propanoic acid and -propanoic acid methyl ester; sulfometuron-methyl; sulfazuron; riazasulfuron; TCA; tebutam; tebuthiuron; terbacil; terbucarb; terbuchlor; terbumeton; terbuthylazine; terbutryne; TFH 450, i.e. N,N-diethyl-3-[(2-ethyl-6-methylphenyl)-sulfonyl]-1H-1,2,4-triazol-1-carboxamide; thiazafluron; thifensulfuron-methyl; thiobencarb; tiocarbaxil; tralkoxydim; tri-allate; triasulfuron; triazofenamide; tribenuron-methyl; triclopyr; tridiphane; trietazine; trifluralin; trimeturon; vernolate; WL 110547, i.e. 5-phenoxy-1-[3-(trifluoromethyl)-phenyl]-1H-tetrazole.

For use, the formulations present in commercially available form are diluted, if appropriate, in a conventional manner, for example using water in the case of wettable powders, emulsifiable concentrates, dispersions and water-dispersible granules. Preparations in the form of dusts and granules for broadcasting or soil application and also sprayable solutions are usually not further diluted with other inert substances before use.

The compounds according to the invention can be applied for example directly to the harmful plants or, post-emergence, to the harmful plants and crop plants simultaneously, or to the area on which the plants grow, for example to arable soils containing seeds of plants or emerged plants, or to areas under cultivation such as, for example, an area on which rice is grown, pre- or post-emergence.

The application rate of the compounds of the formula (I) required varies with the external conditions, such as temperature, humidity and the nature of the herbicide used, amongst others. It can vary within wide limits, for example between 0.001 and 10.0 kg/ha or more of active ingredient, preferably, however, it is between 0.005 and 5 kg/ha.

A. Chemical Examples

EXAMPLES a) 2-Benzylthio-3-nitropyridine 39.1 g (0.315 mol) of benzylmercaptan are introduced into 200 ml of acetonitrile, 47.8 g (0.346 mol) of $K_2CO_3$ are added, and the mixture is stirred for 40 minutes at 60° C. 50.0 g (0.315 mol) of 2-chloro-3-nitropyridine, dissolved in 150 ml of acetonitrile, are subsequently added dropwise and the mixture is refluxed for 4 hours. The acetonitrile is distilled off under reduced pressure, the residue is taken up in dichloromethane, the organic phase is washed in each case once with saturated sodium hydrogen carbonate solution and with 1N hydrochloric acid, the organic phase is dried over magnesium sulfate and the drying agent is filtered off, and the dichloromethane is removed under reduced pressure. Recrystallization from methanol gives 60.9 g (79% of theory) of 2-benzyl3-nitropyridine of melting point 72° C.

b) 3-Nitro-2-pyridine-tert.-butylsulfonamide 24.6 g (0.1 mol) of 2-benzylthio-3-nitropyridine are dissolved in 360 ml of $CH_2Cl_2$. 280 ml of water are added, and 44.9 ml of concentrated HCl are added dropwise at 0° C. 550 ml of 5% sodium hypochlorite solution are subsequently run in at a rate low enough for the internal temperature not to exceed 5° C. After the batch has been stirred for a further 30 minutes at 0° C., it is poured into 500 ml of water, the organic phase is separated off, and the aqueous phase is washed at 0° C. using $CH_2Cl_2$. The combined organic phases are washed with NaCl solution and dried over $MgSO_4$. 32.1 g (0.44 mol) of t-butylamine are subsequently added at −70° C. The batch is allowed to warm to room temperature and poured into water, and the mixture is brought to pH 2–3 using 1N HCl. After the organic phase has been separated off, the aqueous phase is washed with $CH_2Cl_2$, the organic phases are combined and dried, and the solvent is stripped off under reduced pressure. Extraction of the residue by stirring with diethyl ether and filtration gives 14.7 g (57% of theory) of 3-nitro-2-pyridine-tert.-butylsulfonamide of melting point 134° C.

c) 3-Amino-2-pyridine-tert.-butylsulfonamide 14.7 g (0.057 mol) of 3-nitro-2-pyridine-tert.-butylsulfonamide are dissolved in 49 ml of glacial acetic acid and 110 ml of water. 15.8 g (0.28 mol) of iron powder are added slowly at not more than 60° C., and the mixture is stirred for 3 hours at 50° C. When the mixture is cold, the iron oxide is filtered off, and both the aqueous phase and the iron oxide are washed repeatedly using $CH_2Cl_2$. The combined organic phases are dried, and the solvent is stripped off under reduced pressure. 11.2 g (86% of theory) of 3-amino-2-pyridine-tert.-butylsulfonamide of melting point 163° C. are obtained.

d) 3-Formylamino-2-pyridine-tert.-butyl sulfonamide 0.48 g (0.01 mol) of formic acid and 1.3 g (0.013 mol) of acetic anhydride are stirred for 1 hour at 60° C. 1.59 g (0.0069 mol) of 3-amino-2-pyridine-tert.-butylsulfonamide are then added, the mixture is stirred for a further hour at 60° C. and then allowed to cool to room temperature, and extraction by stirring with ether gives 1.50 g (85% of theory) of 3-formylamino-2-pyridine-tert.-butylsulfonamide of melting point 168° C.

e) 3-Formylamino-2-pyridine-sulfonamide 1.50 g (0.0058 mol) of 3-formylamino-2-pyridine-tert.butylsulfonamide are stirred for 4 days at room temperature in 20 ml of anhydrous trifluoroacetic acid. The trifluoroacetic acid is stripped off under reduced pressure, and the residue is extracted by stirring with ether. 1.00 g (85% of theory) of 3-formylamino-2-pyridinesulfonamide of melting point 183° C. are obtained.

f) N-[(4,6-Dimethoxypyrimidin-2-yl)-aminocarbonyl]-3-formyl-amino-2-pyridinesulfonamide (Example 2 of Table 1)

0.75 g (0.0049 mol) of 1,8-diazabicyclo[5.4.0]undec-7-ene (DBU) is added to a solution of 0.5 g (0.0019 mol) of 3-formylamino-2-pyridinesulfonamide and 0.68 g (0.0025 mol) of N-(4,6-dimethoxypyrimidin-2-yl)phenylcarbamate in 40 ml of acetonitrile. The solution is stirred for 16 hours at room temperature, 20 ml of water are subsequently added, and the pH is brought to 4 using 2-normal hydrochloric acid. The mixture is extracted with dichloromethane, the organic phase is dried over $MgSO_4$, and n-heptane is added. Filtration gives 0.64 g (89% of theory) of N-[(4,6-dimethoxypyrimidin-2-yl)-aminocarbonyl]-3-formylamino-2-pyridinesulfonamide of melting point 172° C. (decomp.).

g) N-[(2-Methoxy-4-methyl)-1,3,5-triazin-6-yl)]-aminocarbonyl-3-(N-methyl)acetylamino-2-pyridine-sulfonamide 1.7 ml of a 20% solution of trimethylaluminum in toluene are added dropwise to 1.0 g (0.0044 mol) of 3-(N-methyl)

acetylamino-2-pyridinesulfonamide in 70 ml of dichloromethane. The mixture is stirred for 15 minutes at room temperature, and 0.79 g (0.0044 mol) of methyl-2-methoxy-4-methyl-1,3,5-triazin-6-ylcarbamate, dissolved in 20 ml of dichloromethane, is added, and the mixture is refluxed for 20 hours. The mixture is allowed to cool and poured into 60 ml of ice-cold 1-normal hydrochloric acid, and the aqueous phase is extracted three times using dichloromethane. Drying and stripping off of the solvent give 0.66 g (38% of theory) of N-[(2-methoxy-4-methyl)1,3,5-triazin-6-yl)-aminocarbonyl-3-(N-methylacetylamino)-2-pyridinesulfonamide of melting point 165° C. (decomp.).

The other compounds of Tables 1–3 below are obtained analogously to the processes of Examples a to g.

TABLE 1

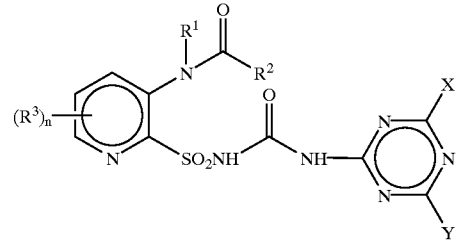

| Ex. | $R^1$ | $R^2$ | $(R^3)_n$ | X | Y | Z | M.p. [° C.] |
|---|---|---|---|---|---|---|---|
| 1 | H | $C_2H_5$ | — | $OCH_3$ | $OCH_3$ | CH | 138 |
| 2 | H | H | — | $OCH_3$ | $OCH_3$ | CH | 172 |
| 3 | H | H | — | $OC_2H_5$ | $OC_2H_5$ | CH | 166 |
| 4 | H | $i$-$C_3H_7$ | — | $OCH_3$ | $OCH_3$ | CH | 165 |
| 5 | H | $CF_3$ | — | $OCH_3$ | $OCH_3$ | CH | 175 |
| 6 | H | $OC_2H_5$ | — | $OCH_3$ | $OCH_3$ | CH | 171 |
| 7 | H | Cyclo-propyl | — | $OCH_3$ | $OCH_3$ | CH | 134 |
| 8 | H | $CH_3$ | — | $CH_3$ | $CH_3$ | CH | 182 |
| 9 | H | $N(CH_3)_2$ | — | $OCH_3$ | $OCH_3$ | CH | 182 |
| 10 | H | Phenyl | — | $OCH_3$ | $OCH_3$ | CH | 186 |
| 11 | H | $CH=CH_2$ | — | $OCH_3$ | $OCH_3$ | CH | 164 |
| 12 | H | Cyclobutyl | — | $OCH_3$ | $OCH_3$ | CH | 157 |
| 13 | H | $CH_2OCH_3$ | — | $OCH_3$ | $OCH_3$ | CH | 192 |
| 14 | H | $CH_2Cl$ | — | $OCH_3$ | $OCH_3$ | CH | 270 |
| 15 | H | $CH_2$—Br | — | $OCH_3$ | $OCH_3$ | CH | 207 |
| 16 | H | $CH_2$—$NO_2$ | — | $OCH_3$ | $OCH_3$ | CH |  |
| 17 | H | $CH_2$—CN | — | $OCH_3$ | $OCH_3$ | CH |  |
| 18 | H | N—$COC_3H_7$ / $C_3H_7$ | — | $OCH_3$ | $OCH_3$ | CH | 180 |
| 19 | $CH_3$ | $CH_3$ | — | $OCH_3$ | $OCH_3$ | CH | 180 |
| 20 | $CH_3$ | $C_2H_5$ | — | $OCH_3$ | $OCH_3$ | CH | 187 |
| 21 | $CH_3$ | $CF_3$ | — | $OCH_3$ | $OCH_3$ | CH | 142 |
| 22 | $CH_3$ | $i$-$C_3H_7$ | — | $OCH_3$ | $OCH_3$ | CH | 168 |
| 23 | $CH_3$ | $CH_3$ | — | $OCH_3$ | $CH_3$ | N | 165 |
| 24 | $CH_3$ | $CH_3$ | — | $CH_3$ | $CH_3$ | CH | 181 |
| 25 | $CH_3$ | $CH_3$ | — | $OCH_3$ | $OCH_3$ | CH | 185 |
| 26 | $CH_3$ | H | — | $OCH_3$ | $OCH_3$ | CH | 178 |
| 27 | $C_2H_5$ | H | — | $OCH_3$ | $CH_3$ | N |  |
| 28 | $CH_3$ | H | — | $OCH_3$ | $CH_3$ | N |  |
| 29 | n-$C_3H_7$ | H | — | $OCH_3$ | $OCH_3$ | CH | 184 |
| 30 | n-$C_3H_7$ | H | — | $OCH_3$ | $CH_3$ | N |  |
| 31 | n-$C_3H_7$ | H | — | $CH_3$ | $CH_3$ | CH |  |
| 32 | n-$C_4H_9$ | H | — | $OCH_3$ | $OCH_3$ | CH | 156 |
| 33 | n-$C_4H_9$ | H | — | $CH_3$ | $CH_3$ | CH |  |
| 34 | n-$C_4H_9$ | H | — | $OCH_3$ | $CH_3$ | N |  |
| 35 | i-$C_4H_9$ | H | — | $OCH_3$ | $OCH_3$ | CH |  |
| 36 | i-$C_4H_9$ | H | — | $CH_3$ | $CH_3$ | CH |  |
| 37 | i-$C_4H_9$ | H | — | $OCH_3$ | $CH_3$ | CH |  |
| 38 | Cyclobutylmethyl | H | — | $OCH_3$ | $OCH_3$ | CH |  |
| 39 | Cyclopropylmethyl | H | — | $OCH_3$ | $OCH_3$ | CH |  |
| 40 | $CH_3$ | $CH=CH_2$ | — | $OCH_3$ | $OCH_3$ | CH |  |
| 41 | $CH_3$ | Phenyl | — | $OCH_3$ | $OCH_3$ | CH |  |
| 42 | $CH_3$ | i-$C_4H_9$ | — | $OCH_3$ | $OCH_3$ | CH | 211 |
| 43 | $CH_3$ | $CH_2$—O—$CH_3$ | — | $OCH_3$ | $OCH_3$ | CH |  |
| 44 | $CH_3$ | $CH_2$—Cl | — | $OCH_3$ | $OCH_3$ | CH |  |
| 45 | $CH_3$ | $CH_2$—Br | — | $OCH_3$ | $OCH_3$ | CH |  |
| 46 | $CH_3$ | $CH_2$—$NO_2$ | — | $OCH_3$ | $OCH_3$ | CH |  |
| 47 | $CH_3$ | $CH_2$—CN | — | $OCH_3$ | $OCH_3$ | CH |  |
| 48 | $CH_2CF_3$ | $CH_3$ | — | $OCH_3$ | $OCH_3$ | CH |  |
| 49 | $CH_2CF_3$ | $CF_3$ | — | $OCH_3$ | $OCH_3$ | CH |  |
| 50 | $CH_2CF_3$ | H | — | $OCH_3$ | $OCH_3$ | CH |  |

TABLE 1-continued

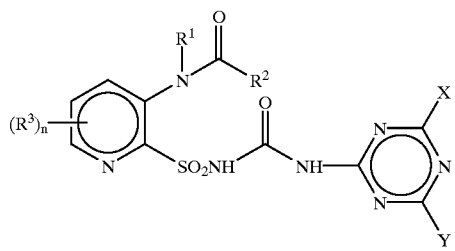

| Ex. | R$^1$ | R$^2$ | (R$^3$)$_n$ | X | Y | Z | M.p. [° C.] |
|---|---|---|---|---|---|---|---|
| 51 | Benzyl | CH$_3$ | — | OCH$_3$ | OCH$_3$ | CH | |
| 52 | Benzyl | CF$_3$ | — | OCH$_3$ | OCH$_3$ | CH | |
| 53 | Benzyl | H | — | OCH$_3$ | OCH$_3$ | CH | |
| 54 | CH$_3$ | CH=CH$_2$ | — | CH$_3$ | CH$_3$ | CH | |
| 55 | CH$_3$ | Phenyl | — | CH$_3$ | CH$_3$ | CH | |
| 56 | CH$_3$ | i-C$_4$H$_9$ | — | CH$_3$ | CH$_3$ | CH | |
| 57 | CH$_3$ | CH$_2$—OCH$_3$ | — | CH$_3$ | CH$_3$ | CH | |
| 58 | CH$_3$ | CH$_2$—Cl | — | CH$_3$ | CH$_3$ | CH | |
| 59 | CH$_3$ | CH$_2$—Br | — | CH$_3$ | CH$_3$ | CH | |
| 60 | CH$_3$ | CH$_2$NO$_2$ | — | CH$_3$ | CH$_3$ | CH | |
| 61 | CH$_3$ | CH$_2$—CN | — | CH$_3$ | CH$_3$ | CH | |
| 62 | CH$_2$—CF$_3$ | CH$_3$ | — | CH$_3$ | CH$_3$ | CH | |
| 63 | CH$_2$—CF$_3$ | CF$_3$ | — | CH$_3$ | CH$_3$ | CH | |
| 64 | CH$_2$—CF$_3$ | H | — | CH$_3$ | CH$_3$ | CH | |
| 65 | Benzyl | CH$_3$ | — | CH$_3$ | CH$_3$ | CH | |
| 66 | Benzyl | CF$_3$ | — | CH$_3$ | CH$_3$ | CH | |
| 67 | Benzyl | H | — | CH$_3$ | CH$_3$ | CH | |
| 68 | CH$_3$ | CH=CH$_2$ | — | OCH$_3$ | CH$_3$ | N | |
| 69 | CH$_3$ | Phenyl | — | OCH$_3$ | CH$_3$ | N | |
| 70 | CH$_3$ | i-C$_4$H$_9$ | — | OCH$_3$ | CH$_3$ | N | |
| 71 | CH$_3$ | CH$_2$—OCH$_3$ | — | OCH$_3$ | CH$_3$ | N | |
| 72 | CH$_3$ | CH$_2$—Cl | — | OCH$_3$ | CH$_3$ | N | |
| 73 | CH$_3$ | CH$_2$—Br | — | OCH$_3$ | CH$_3$ | N | |
| 74 | CH$_3$ | CH$_2$—NO$_2$ | — | OCH$_3$ | CH$_3$ | N | |
| 75 | CH$_3$ | CH$_2$—CN | — | OCH$_3$ | CH$_3$ | N | |
| 76 | CH$_2$—CF$_3$ | CH$_3$ | — | OCH$_3$ | CH$_3$ | N | |
| 77 | CH$_2$—CF$_3$ | CF$_3$ | — | OCH$_3$ | CH$_3$ | N | |
| 78 | CH$_2$—CF$_3$ | H | — | OCH$_3$ | CH$_3$ | N | |
| 79 | Benzyl | CH$_3$ | — | OCH$_3$ | CH$_3$ | N | |
| 80 | Benzyl | CF$_3$ | — | OCH$_3$ | CH$_3$ | N | |
| 81 | Benzyl | H | — | OCH$_3$ | CH$_3$ | N | |
| 82 | C$_2$H$_5$ | CH$_3$ | — | OCH$_3$ | OCH$_3$ | CH | 185 |
| 83 | C$_2$H$_5$ | CH$_3$ | — | CH$_3$ | CH$_3$ | CH | |
| 84 | C$_2$H$_5$ | CH$_3$ | — | OCH$_3$ | CH$_3$ | N | |
| 85 | C$_2$H$_5$ | H | — | CH$_3$ | CH$_3$ | CH | |
| 86 | C$_2$H$_5$ | CF$_3$ | — | OCH$_3$ | OCH$_3$ | CH | 190 |
| 87 | C$_2$H$_5$ | CF$_3$ | — | CH$_3$ | CH$_3$ | CH | |
| 88 | C$_2$H$_5$ | CF$_3$ | — | OCH$_3$ | CH$_3$ | N | |
| 89 | C$_2$H$_5$ | CH=CH$_2$ | — | OCH$_3$ | OCH$_3$ | CH | |
| 90 | C$_2$H$_5$ | CH=CH$_2$ | — | CH$_3$ | CH$_3$ | CH | |
| 91 | C$_2$H$_5$ | CH=CH$_2$ | — | OCH$_3$ | CH$_3$ | N | |
| 92 | C$_2$H$_5$ | CH$_2$—OCH$_3$ | — | OCH$_3$ | OCH$_3$ | CH | |
| 93 | C$_2$H$_5$ | CH$_2$—OCH$_3$ | — | CH$_3$ | CH$_3$ | CH | |
| 94 | C$_2$H$_5$ | CH$_2$—O—CH$_3$ | — | OCH$_3$ | CH$_3$ | N | |
| 95 | C$_2$H$_5$ | CH$_2$—Cl | — | OCH$_3$ | OCH$_3$ | CH | |
| 96 | C$_2$H$_5$ | CH$_2$—Cl | — | CH$_3$ | CH$_3$ | CH | |
| 97 | C$_2$H$_5$ | CH$_2$—Cl | — | OCH$_3$ | CH$_3$ | N | |
| 98 | C$_2$H$_5$ | CH$_2$—Br | — | OCH$_3$ | OCH$_3$ | CH | |
| 99 | C$_2$H$_5$ | CH$_2$—Br | — | CH$_3$ | CH$_3$ | CH | |
| 100 | C$_2$H$_5$ | CH$_2$—Br | — | OCH$_3$ | CH$_3$ | N | |
| 101 | C$_2$H$_5$ | CH$_2$—NO$_2$ | — | OCH$_3$ | OCH$_3$ | CH | |
| 102 | C$_2$H$_5$ | CH$_2$—NO$_2$ | — | CH$_3$ | CH$_3$ | CH | |
| 103 | C$_2$H$_5$ | CH$_2$—NO$_2$ | — | OCH$_3$ | CH$_3$ | N | |
| 104 | C$_2$H$_5$ | CH$_2$—CN | — | OCH$_3$ | OCH$_3$ | CH | |
| 105 | C$_2$H$_5$ | CH$_2$—CN | — | CH$_3$ | CH$_3$ | CH | |
| 106 | C$_2$H$_5$ | CH$_2$—CN | — | OCH$_3$ | CH$_3$ | N | |
| 107 | C$_2$H$_5$ | i-C$_4$H$_9$ | — | OCH$_3$ | OCH$_3$ | CH | |
| 108 | C$_2$H$_5$ | i-C$_4$H$_9$ | — | CH$_3$ | CH$_3$ | CH | |
| 109 | C$_2$H$_5$ | i-C$_4$H$_9$ | — | OCH$_3$ | CH$_3$ | N | |
| 110 | H | C$_2$H$_5$ | 6-CH$_3$ | OCH$_3$ | OCH$_3$ | CH | |
| 111 | H | H | 6-CH$_3$ | OCH$_3$ | OCH$_3$ | CH | |
| 112 | H | H | 6-CH$_3$ | OC$_2$H$_5$ | OC$_2$H$_5$ | CH | |
| 113 | H | i-C$_3$H$_7$ | 6-CH$_3$ | OCH$_3$ | OCH$_3$ | CH | |
| 114 | H | CF$_3$ | 6-CH$_3$ | OCH$_3$ | OCH$_3$ | CH | |

TABLE 1-continued

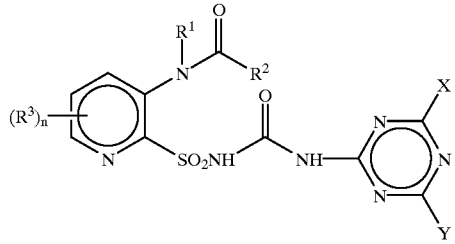

| Ex. | R$^1$ | R$^2$ | (R$^3$)$_n$ | X | Y | Z | M.p. [° C.] |
|---|---|---|---|---|---|---|---|
| 115 | H | OC$_2$H$_5$ | 6-CH$_3$ | OCH$_3$ | OCH$_3$ | CH | |
| 116 | H | Cyclopropyl | 6-CH$_3$ | OCH$_3$ | OCH$_3$ | CH | |
| 117 | H | CH$_3$ | 6-CH$_3$ | CH$_3$ | CH$_3$ | CH | |
| 118 | H | N(CH$_3$)$_2$ | 6-CH$_3$ | OCH$_3$ | OCH$_3$ | CH | |
| 119 | H | Phenyl | 6-CH$_3$ | OCH$_3$ | OCH$_3$ | CH | |
| 120 | H | CH=CH$_2$ | 6-CH$_3$ | OCH$_3$ | OCH$_3$ | CH | |
| 121 | H | Cyclobutyl | 6-CH$_3$ | OCH$_3$ | OCH$_3$ | CH | |
| 122 | H | CH$_2$—O—CH$_3$ | 6-CH$_3$ | OCH$_3$ | OCH$_3$ | CH | |
| 123 | H | CH$_2$—Cl | 6-CH$_3$ | OCH$_3$ | OCH$_3$ | CH | |
| 124 | H | CH$_2$—Br | 6-CH$_3$ | OCH$_3$ | OCH$_3$ | CH | |
| 125 | H | CH$_2$—CN | 6-CH$_3$ | OCH$_3$ | OCH$_3$ | CH | |
| 126 | CH$_3$ | CH$_3$ | 6-CH$_3$ | OCH$_3$ | OCH$_3$ | CH | |
| 127 | CH$_3$ | C$_2$H$_5$ | 6-CH$_3$ | OCH$_3$ | OCH$_3$ | CH | |
| 128 | CH$_3$ | CF$_3$ | 6-CH$_3$ | OCH$_3$ | OCH$_3$ | CH | |
| 129 | CH$_3$ | i-C$_3$H$_7$ | 6-CH$_3$ | OCH$_3$ | OCH$_3$ | CH | |
| 130 | CH$_3$ | CH$_3$ | 6-CH$_3$ | OCH$_3$ | CH$_3$ | N | |
| 131 | CH$_3$ | CH$_3$ | 6-CH$_3$ | CH$_3$ | CH$_3$ | CH | |
| 132 | C$_2$H$_5$ | H | 6-CH$_3$ | OCH$_3$ | OCH$_3$ | CH | |
| 133 | CH$_3$ | H | 6-CH$_3$ | OCH$_3$ | OCH$_3$ | CH | |
| 134 | C$_2$H$_5$ | H | 6-CH$_3$ | OCH$_3$ | CH$_3$ | N | |
| 135 | CH$_3$ | H | 6-CH$_3$ | OCH$_3$ | CH$_3$ | N | |
| 136 | n-C$_3$H$_7$ | H | 6-CH$_3$ | OCH$_3$ | OCH$_3$ | CH | |
| 137 | n-C$_3$H$_7$ | H | 6-CH$_3$ | OCH$_3$ | CH$_3$ | N | |
| 138 | n-C$_4$H$_9$ | H | 6-CH$_3$ | OCH$_3$ | OCH$_3$ | CH | |
| 139 | n-C$_4$H$_9$ | H | 6-CH$_3$ | CH$_3$ | CH$_3$ | CH | |
| 140 | n-C$_4$H$_9$ | H | 6-CH$_3$ | OCH$_3$ | CH$_3$ | N | |
| 141 | i-C$_4$H$_9$ | H | 6-CH$_3$ | OCH$_3$ | OCH$_3$ | CH | |
| 142 | i-C$_4$H$_9$ | H | 6-CH$_3$ | CH$_3$ | CH$_3$ | CH | |
| 143 | i-C$_4$H$_9$ | H | 6-CH$_3$ | OCH$_3$ | CH$_3$ | N | |
| 144 | Cyclobutylmethyl | H | 6-CH$_3$ | OCH$_3$ | OCH$_3$ | CH | |
| 145 | Cyclopropylmethyl | H | 6-CH$_3$ | OCH$_3$ | OCH$_3$ | CH | |
| 146 | CH$_3$ | CH=CH$_2$ | 6-CH$_3$ | OCH$_3$ | OCH$_3$ | CH | |
| 147 | CH$_3$ | CH$_2$—O—CH$_3$ | 6-CH$_3$ | OCH$_3$ | OCH$_3$ | CH | |
| 148 | CH$_2$—CF$_3$ | CH$_3$ | 6-CH$_3$ | OCH$_3$ | OCH$_3$ | CH | |
| 149 | CH$_2$—CF$_3$ | CF$_3$ | 6-CH$_3$ | OCH$_3$ | OCH$_3$ | CH | |
| 150 | CH$_2$—CF$_3$ | H | 6-CH$_3$ | OCH$_3$ | OCH$_3$ | CH | |
| 151 | H | H | 6-Cl | OCH$_3$ | OCH$_3$ | CH | |
| 152 | CH$_3$ | H | 6-Cl | OCH$_3$ | OCH$_3$ | CH | |
| 153 | C$_2$H$_5$ | H | 6-Cl | OCH$_3$ | OCH$_3$ | CH | |
| 154 | n-C$_3$H$_7$ | H | 6-Cl | OCH$_3$ | OCH$_3$ | CH | |
| 155 | n-C$_4$H$_9$ | H | 6-Cl | OCH$_3$ | OCH$_3$ | CH | |
| 156 | H | CH$_3$ | 6-Cl | OCH$_3$ | OCH$_3$ | CH | |
| 157 | H | C$_2$H$_5$ | 6-Cl | OCH$_3$ | OCH$_3$ | CH | |
| 158 | H | i-C$_3$H$_7$ | 6-Cl | OCH$_3$ | OCH$_3$ | CH | |
| 159 | H | Phenyl | 6-Cl | OCH$_3$ | OCH$_3$ | CH | |
| 160 | H | CH=CH$_2$ | 6-Cl | OCH$_3$ | OCH$_3$ | CH | |
| 161 | H | CH$_2$—OCH$_3$ | 6-Cl | OCH$_3$ | OCH$_3$ | CH | |
| 162 | H | CH$_2$—Cl | 6-Cl | OCH$_3$ | OCH$_3$ | CH | |
| 163 | H | CF$_3$ | 6-Cl | OCH$_3$ | OCH$_3$ | CH | |
| 164 | H | CH$_2$—CN | 6-Cl | OCH$_3$ | OCH$_3$ | CH | |
| 165 | H | CH$_2$—NO$_2$ | 6-Cl | OCH$_3$ | OCH$_3$ | CH | |
| 166 | CH$_3$ | CH$_3$ | 6-Cl | OCH$_3$ | OCH$_3$ | CH | |
| 167 | CH$_3$ | CF$_3$ | 6-Cl | OCH$_3$ | OCH$_3$ | CH | |
| 168 | CH$_3$ | H | 6-CF$_3$ | OCH$_3$ | OCH$_3$ | CH | |
| 169 | CH$_3$ | CH$_2$—OCH$_3$ | 6-Cl | OCH$_3$ | OCH$_3$ | CH | |
| 170 | C$_2$H$_5$ | H | 6-CF$_3$ | OCH$_3$ | OCH$_3$ | CH | |
| 171 | C$_2$H$_5$ | CH$_3$ | 6-Cl | OCH$_3$ | OCH$_3$ | CH | |
| 172 | C$_2$H$_5$ | CF$_3$ | 6-Cl | OCH$_3$ | OCH$_3$ | CH | |
| 173 | C$_2$H$_5$ | CH$_2$—OCH$_3$ | 6-Cl | OCH$_3$ | OCH$_3$ | CH | |
| 174 | H | H | 6-OCH$_3$ | OCH$_3$ | OCH$_3$ | CH | |
| 175 | CH$_3$ | H | 6-OCH$_3$ | OCH$_3$ | OCH$_3$ | CH | |
| 176 | C$_2$H$_5$ | H | 6-OCH$_3$ | OCH$_3$ | OCH$_3$ | CH | |
| 177 | H | CH$_3$ | 6-OCH$_3$ | OCH$_3$ | OCH$_3$ | CH | |
| 178 | H | C$_2$H$_5$ | 6-OCH$_3$ | OCH$_3$ | OCH$_3$ | CH | |

TABLE 1-continued

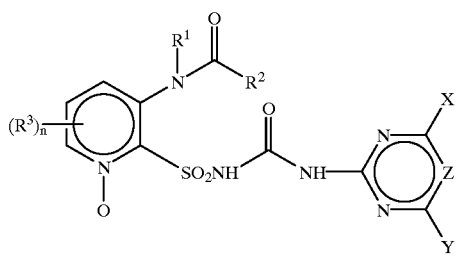

| Ex. | R¹ | R² | (R³)ₙ | X | Y | Z | M.p. [° C.] |
|---|---|---|---|---|---|---|---|
| 179 | H | CF₃ | 6-OCH₃ | OCH₃ | OCH₃ | CH | |
| 180 | CH₂CF₃ | H | 6-OCH₃ | OCH₃ | OCH₃ | CH | |
| 181 | CH₂CF₃ | CH₃ | 6-OCH₃ | OCH₃ | OCH₃ | CH | |
| 182 | H | CH=CH₂ | 6-OCH₃ | OCH₃ | OCH₃ | CH | |
| 183 | CH₃ | CH₃ | 6-CF₃ | OCH₃ | OCH₃ | CH | |
| 184 | CH₃ | CH₃ | — | OCHF₂ | OCHF₂ | CH | |
| 185 | CH₃ | CH₃ | 6-Cl | OCHF₂ | OCHF₂ | CH | |
| 186 | C₂H₅ | H | — | OC₂H₅ | OC₂H₅ | CH | 147 |
| 187 | H | CO—OCH₃ | — | OCH₃ | OCH₃ | CH | 144 |
| 188 | H | CHCl₂ | — | OCH₃ | OCH₃ | CH | 116 |
| 189 | H | CCl=CCl₂ | — | OCH₃ | OCH₃ | CH | 174 |
| 190 | H | CCl=CCl₂ | — | CH₃ | CH₃ | CH | 241 |
| 191 | CH₃ | CF₃ | — | CH₃ | CH₃ | CH | 186 |
| 192 | CH₃ | OC₂H₅ | — | OCH₃ | OCH₃ | CH | 175 |
| 193 | H | OC₂H₅ | 6-F | OCH₃ | OCH₃ | CH | 176 |
| 194 | H | i-C₃H₇ | 6-F | OCH₃ | OCH₃ | CH | 187 |
| 195 | CH₃ | Cyclopropyl | — | OCH₃ | OCH₃ | CH | 187 |
| 196 | H | CCl₃ | — | OCH₃ | OCH₃ | CH | 160 |
| 197 | CH₃ | Cyclobutyl | — | OCH₃ | OCH₃ | CH | 207 |
| 198 | CH₂—OCH₃ | H | — | OCH₃ | OCH₃ | CH | 128 |
| 199 | H | OCH₃ | — | OCH₃ | OCH₃ | CH | 200 |
| 200 | C₂H₅ | CCl₃ | — | OCH₃ | OCH₃ | CH | 196 |
| 201 | CH₃ | OCH₃ | — | OCH₃ | OCH₃ | CH | 178 |
| 202 | CH₃ | CH₂Cl—C(CH₃)₂Cl | — | OCH₃ | OCH₃ | CH | 222 |
| 203 | H | CH₂Cl—C(CH₃)₂Cl | — | OCH₃ | OCH₃ | CH | 175 |
| 204 | H | NC₂H₅ | — | OCH₃ | OCH₃ | CH | 132 |
| 205 | C₂H₅ | OCH₃ | — | OCH₃ | OCH₃ | CH | 199 |
| 206 | C₂H₅ | CHCl₂ | — | OCH₃ | OCH₃ | CH | 181 |
| 207 | CH₃ | CHCl₂ | — | OCH₃ | OCH₃ | CH | 176 |
| 208 | H | CH₂—(CF₂)₃CF₃ | — | OCH₃ | OCH₃ | CH | 239 |
| 209 | CH₃ | CCl=CCl₂ | — | OCH₃ | OCH₃ | CH | 143 |

TABLE 2

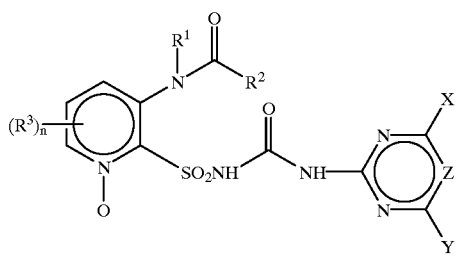

| Example | R¹ | R² | (R³)ₙ | X | Y | Z | M.p. |
|---|---|---|---|---|---|---|---|
| 210 | H | H | — | OCH₃ | OCH₃ | CH | |
| 211 | H | CH₃ | — | OCH₃ | OCH₃ | CH | |
| 212 | H | CH₂CH₃ | — | OCH₃ | OCH₃ | CH | |
| 213 | H | CH₂CH(CH₃)₂ | — | OCH₃ | OCH₃ | CH | |
| 214 | H | CF₃ | — | OCH₃ | OCH₃ | CH | |
| 215 | CH₃ | H | — | OCH₃ | OCH₃ | CH | |
| 216 | CH₃ | CH₃ | — | OCH₃ | OCH₃ | CH | |

TABLE 2-continued

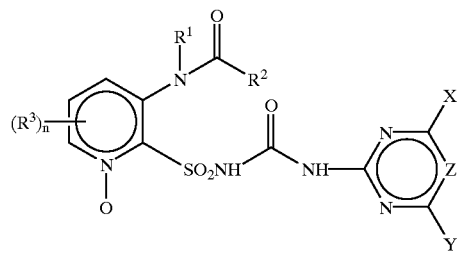

| Example | R¹ | R² | (R³)ₙ | X | Y | Z | M.p. |
|---|---|---|---|---|---|---|---|
| 217 | CH₃ | CH₂CH₃ | — | OCH₃ | OCH₃ | CH | |
| 218 | CH₃ | CH₂CH(CH₃)₂ | — | OCH₃ | OCH₃ | CH | |
| 219 | C₂H₅ | H | — | OCH₃ | OCH₃ | CH | |
| 220 | C₂H₅ | CH₃ | — | OCH₃ | OCH₃ | CH | |
| 221 | C₂H₅ | C₂H₅ | — | OCH₃ | OCH₃ | CH | |
| 222 | C₂H₅ | CF₃ | — | OCH₃ | OCH₃ | CH | |

TABLE 3

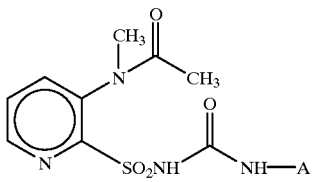

| Example | A | M.p. |
|---|---|---|
| 223 | (4-OCH₃, 2-methyl furo[2,3-b]pyridine group) | |
| 224 | (4-OCH₃, 2-methyl pyrano[2,3-b]pyridine group) | |
| 225 | (4-OCH₃, 2-methyl furo[2,3-b]pyridine group) | |
| 226 | (1-CH₃, 5-OCH₃ triazole group) | |
| 227 | (–CH₂– linked 4-OCH₃, 6-CH₃ pyrimidine) | |
| 228 | (3-CN, 4-CH₃, 6-OCH₃ pyridine) | |
| 229 | (2-OCH₃, 5-Cl pyridine) | |

TABLE 4

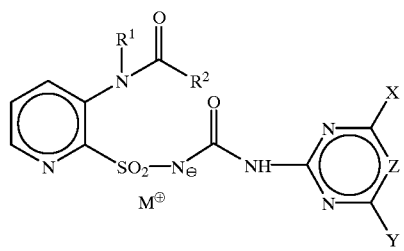

| Example | R¹ | R² | M⊕ | X | Y | Z | M.p. |
|---|---|---|---|---|---|---|---|
| 230 | CH₃ | i-C₃H₇ | Na+ | OCH₃ | OCH₃ | CH | 191° C. |
| 231 | C₂H₅ | H | Na+ | OCH₃ | OCH₃ | CH | |
| 232 | CH₃ | CH₃ | NH₄+ | OCH₃ | OCH₃ | CH | |
| 233 | CH₃ | CH₃ | Na+ | OCH₃ | OCH₃ | CH | |
| 234 | C₂H₅ | H | NH₄+ | OCH₃ | OCH₃ | CH | |
| 235 | C₂H₅ | CH₃ | Li+ | OCH₃ | OCH₃ | CH | |
| 236 | C₂H₅ | H | K+ | OCH₃ | OCH₃ | CH | |
| 237 | CH₃ | CF₃ | Na+ | OCH₃ | OCH₃ | CH | |

B. Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium ligninsulfonate and 1 part by weight of sodium oleoylmethyltaurate as wetting and dispersing agent and grinding the mixture in a pinned disk mill.

c) A dispersion concentrate which is readily dipersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 up to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.

e) Water-dispersible granules are obtained by mixing 75 parts by weight of a compound of the formula (I),
10 parts by weight of calcium ligninsulfonate,
5 parts by weight of sodium lauryl sulfate,
3 parts by weight of polyvinyl alcohol and
7 parts by weight of kaolin, grinding the mixture in a pinned disk mill and granulating the powder in a fluidized bed by spraying on water as granulation liquid.

f) Water-dispersible granules are also obtained by homogenizing and precomminuting 25 parts by weight of a compound of the formula (I),
5 parts by weight of sodium 2,2'-dinaphthylmethane-6,6'-disulfonate,
2 parts by weight of sodium oleolythyltaurate, -continued 1 part by weight of polyvinyl alcohol,
17 parts by weight of calciun carbonate and
50 parts by weight of water in a colloid mill, subsequently grinding the mixture in a bead mill and atomizing and drying the resulting suspension in a spray tower by means of a single-substance nozzle C. Biological Examples 1. Pre-emergence effect on weeds Seeds or rhizome pieces of monocotyledon and dicotyledon weed plants were placed in sandy loam soil in plastic pots and covered with soil. The compounds according to the invention which were formulated in the form of wettable powders or emulsion concentrates were then applied to the surface of the soil cover in the form of an aqueous suspension or emulsion at an application rate of 600 to 800 l of water/ha (converted), in various dosages.

After the treatment, the pots were placed in a greenhouse and kept under good growth conditions for the weeds. After the test plants had emerged, the damage to the plants or the negative effect on the emergence was scored visually after a test period of 3 to 4 weeks by comparison with untreated controls. As shown by the test results, the compounds according to the invention have a good herbicidal pre-emergence action against a broad range of grass weeds and dicotyledon weeds. For example, the compounds of Examples 1, 2, 3, 4, 5, 6, 7, 8, 9, 10, 11, 12, 13, 14, 15, 18, 19, 20, 21, 22, 24, 25, 26, 29, 32, 42, 82, 86, 186–209 and 230 have a very good herbicidal action against harmful plants such as *Sinapis alba, Chrysanthemum segetum, Avena sativa, Stellaria media, Echinochloa crus-galli, Lolium multiflorum*, Setaria spp., *Abutilon theophrasti, Amaranthus retroflexus* and *Panicum miliaceum* when used pre-emergence at an application rate of 0.3 kg of active ingredient per hectare and less.

2. Post-emergence effect on weeds

Seeds or rhizome pieces of monocotyledon and dicotyledon weeds were placed in sandy loam soil in plastic pots, covered with soil and grown in a greenhouse under good growth conditions. Three weeks after sowing, the test plants were treated in the three-leaf stage.

The compounds according to the invention which were formulated as wettable powders or as emulsion concentrates were sprayed at various dosage rates on the green parts of the plants at an application rate of 600 to 800 l of water/ha (converted) and, after the test plants had remained in the greenhouse for about 3 to 4 weeks under ideal growth conditions, the effect of the preparations was scored visually by comparison with untreated controls. The agents according to the invention also have a good herbicidal post-emergence action against a broad range of economically important grass weeds and dicotyledon weeds. For example, the compounds of Examples 1, 2, 3, 4, 5, 6, 7, 8, 9, 10, 11, 12, 13, 14, 15, 18, 19, 20, 21, 22, 24, 25, 26, 29, 32, 42, 82, 86, 186–209 and 230 have very good herbicidal action against harmful plants such as *Sinapis alba, Stellaria media, Echinochloa crus-galli, Lolium multiflorum, Chrysanthemum segetum*, Setaria spp., *Abutilon theophrasti, Amaranthus retroflexus* and *Panicum miliaceum*, and *Avena sativa*, when used post-emergence at an application rate of 0.3 kg of active ingredient per hectare and less.

What is claimed is:

1. A Compound of the formula (I) or a salt thereof,

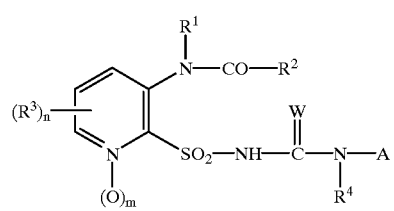

in which $R^1$ is H, $(C_1-C_6)$alkyl which is unsubstituted or substituted by one or more radicals selected from the group consisting of halogen, nitro, $(C_1-C_4)$alkoxy, $(C_3-C_6)$cycloalkyl, aryl and substituted aryl, or aryl in which the aryl radical is unsubstituted or substituted by one or more radicals selected from the group consisting of halogen, nitro, $(C_1-C_4)$alkyl, $(c_1-C_4)$-haloalkyl and $(C_1-C_4)$alkoxy, $R^2$ is H, $(C_1-C_6)$alkyl, $(C_2-C_6)$alkenyl or $(C_2-C_6)$alkynyl, each of the three last-mentioned radicals being unsubstituted or substituted by one or more radicals selected from the group consisting of halogen, $(C_1-C_4)$alkoxy, $(C_1-C_4)$alkylthio, $(C_1-C_4)$alkylsulfynyl, $(C_1-C_4)$alkylsulfonyl, nitro, cyano and thiocyanato, or $(C_1-C_6)$alkoxy or $(C_1C_6)$alkylthio, the last-mentioned 2 radicals being unsubstituted or substituted by one or more radicals selected from the group consisting of halogen, $(C_1-C_4)$alkoxy, $(C_1C_4)$alkylthio, aryl and substituted aryl, $(C_3-C_7)$-cycloalkyl or $(C_3-C_7)$cycloalkoxy, the last-mentioned 2 radicals being unsubstituted or substituted by one or more radicals selected from the group consisting of $(C_1-C_4)$alkyl, $(C_1-C_4)$alkoxy, $(C_1-C_4)$alkylthio, $(C_1-C_4)$haloalkyl and halogen, or aryl, substituted aryl, or a radical of the formula $NR^aR^b$, $R^3$ is $(C_1-C_4)$alkyl, $(C_1-C_3)$haloalkyl, halogen, $NO_2$, CN, $(C_1-C_4)$-alkoxy, $(C_1-C_3)$haloalkoxy, $(C_1-C_3)$-alkylthio, $(C_1-C_3)$alkoxy-$(C_1-C_3)$alkyl, $[(C_1-C_3)$-alkoxy]-carbonyl, $(C_1-C_3)$alkylamino, di$[(C_1-C_3)$-alkyl]-amino, $(C_1-C_6)$alkylsulfynyl, $(C_1-C_3)$-alkylsuflonyl, $SO_2NR^cR^d$ or $C(O)NR^eR^f$, $R^a$, $R^b$, $R^c$, $R^d$, $R^e$ and $R^f$ independently of one another are H, $(C_1-C_4)$alkyl, $(C_3-C_6)$alkenyl, $(C_3-C_6)$alkynyl, $[(C_1-C_4)$alkyl]-carbonyl, arylcarbonyl, which is unsubstituted or substituted in the aryl radical, or the pairs $R^a$ and $R^b$, $R^c$ and $R^d$ or $R^e$ and $R^f$ together with the N atom linking them are a heterocyclic saturated or unsaturated ring selected from the group consisting of pyrrole, imidazole, pyrazole, triazole, pyrrazolone, oxazole, oxazolene, propane sultams, butane sultams, pyrrolidone, piperidine and morpholine, $R^4$ is H or $(C_1-C_4)$alkyl, m is 0 or 1, n is 0, 1 or 2, A is a radical of the formula

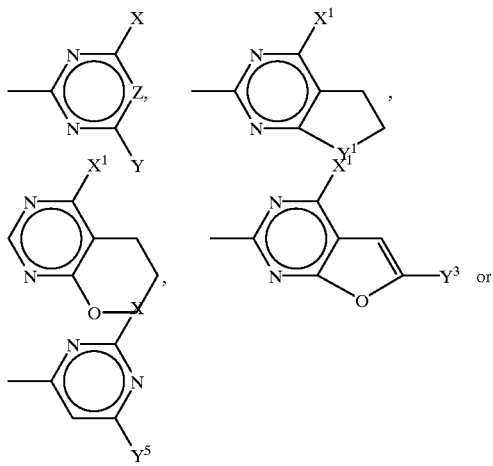

X and Y independently of one another are H, halogen, $(C_1-C_3)$alkyl, $(C_1-C_3)$alkoxy or $(C_1-C_3)$alkylthio, the abovementioned alkyl-containing radicals being unsubstituted or mono- or polysubstituted by halogen or mono- disubstituted by $(C_1-C_3)$-alkoxy or $(C_1-C_3)$ alkylthio, or a radical of the formula $NR^5R^6$, $(C_3-C_6)$ cycloalkyl, $(C_2-C_4)$alkenyl, $(C_2-C_4)$alkynyl, $(C_3-C_4)$ alkenyloxy or $(C_3-C_4)$alkynyloxy, $R^5$ and $R^6$ independently of one another are H, $(C_1-C_3)$ alkyl or $(C_3-C_4)$alkenyl, W is O or S, Z is CH, $X^1$ is $CH_3$, $OCH_3$, $OC_2H_5$ or $OCF_2H$, $Y^1$ is —O— or —$CH_2$—, $Y^3$ is H or $CH_3$, $Y^5$ is $CH_3$, $C_2H_5$ or Cl.

2. A compound or a salt thereof, as claimed in claim 1, wherein $R^1$ is H, $(C_1-C_4)$alkyl which is unsubstituted or substituted by 1 to 3 radicals selected from the group comprising halogen or by $(C_1-C_2)$alkoxy or $(C_3-C_5)$ cycloalkyl, or $R^2$ is H, $(C_1-C_4)$alkyl which is unsubstituted or substituted by one or more halogen atoms or by $(C_1-C_2)$ alkoxy, or $(C_2-C_4)$alkenyl, $(C_2-C_3)$alkynyl, $(C_3-C_5)$ cycloalkyl, $(C_1-C_4)$alkoxy which is unsubstituted or substituted by one or more halogen atoms or by phenyl, or a radical of the formula $NR^aR^b$ in which $R^a$ and $R^b$ independently of one another are H or $(C_1-C_4)$alkyl, or $R^3$ is $(C_1-C_4)$alkyl, $(C_1-C_3)$haloalkyl, halogen, $(C_1-C_3)$ alkoxy or nitro, or A is a radical of the formula

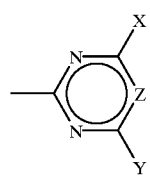

in which one of the radicals X and Y is $(C_1-C_3)$-alkyl, $(C_1-C_3)$alkoxy, $(C_1-C_3)$haloalkyl, $(C_1-C_3)$-haloalkoxy or $[(C_1-C_2)$alkoxy$]$-$(C_1-C_2)$alkyl and the other radical Y or X is $(C_1-C_3)$alkyl, $(C_1-C_3)$alkoxy or $(C_1-C_3)$ alkylthio, where each of the last-mentioned 3 radicals is unsubstituted or mono- or polysubstituted by halogen or mono- or disubstituted by $(C_1-C_3)$alkoxy or $(C_1-C_3)$-alkylthio, or halogen, or a radical of the formula $NR^5R^6$ in which $R^5$ and $R^6$ independently of one another are H, $(C_1-C_3)$alkyl or $(C_3-C_4)$-alkenyl, or $(C_3-C_6)$cycloalkyl, $(C_2-C_4)$alkenyl, $(C_2-C_4)$alkynyl, $(C_3-C_4)$alkenyloxy or $(C_3-C_4)$alkynyloxy.

3. A compound or a salt thereof, as claimed in claim 1, wherein $R^1$ is H, $(C_1-C_4)$alkyl, $(C_1-C_4)$haloalkyl or $[(C_1-C_2)$-alkoxy$]$-$(C_1-C_2)$alkyl, $R^2$ is H, $(C_1-C_4)$alkyl, halo-$(C_1-C_4)$alkyl, $(C_2-C_4)$-alkenyl, $(C_2-C_4)$alkynyl, $(C_1-C_4)$alkoxy, $[(C_1-C_2)$ alkoxy$]$-$(C_1-C_2)$alkyl, $(C_3-C_5)$cycloalkyl or a radical of the formula $NR^aR^b$ in which $R^a$ and $R^b$ independently of one another are H or $(C_1-C_4)$-alkyl, $R^3$ is $(C_1-C_4)$alkyl, halogen, nitro or $(C_1-C_4)$alkoxy and n is 0 or 1.

4. A compound or a salt thereof, according to claim 1, wherein one of the radicals X or Y is $(C_1-C_2)$alkyl, $(C_1-C_2)$-alkoxy or $OCF_2H$ and the other radical Y or X is $(C_1-C_2)$alkyl, $(C_1-C_2)$alkoxy, halogen, $OCF_2H$, $OCH_2CF_3$ or $CF_3$.

5. A herbicidal or plant-growth-regulating agent, which comprises at least one compound of the formula (I) or a salt thereof as claimed in claim 1, and formulation auxiliaries which are customary in crop protection.

6. A method of controlling harmful plants or for regulating the growth of plants, which comprises applying an effective amount of at least one compound of the formula (I) or a salt thereof as claimed in claim 1, to the harmful plants or plants, to the seeds of these plants, or to the area on which the plants grow.

7. A method of controlling harmful plants wherein a compound of the formula (I) or a salt thereof as claimed in claim 1 is used as a herbicide.

8. A compound or a salt thereof, as claimed in claim 1, wherein $R^1$ is H, $CH_3$ or $C_2H_5$, $R^2$ is H, $(C_1-C_4)$-alkyl, $(C_1-C_2)$-haloalkyl, vinyl, cyclopropyl, cyclobutyl, $(C_1-C_2)$-alkoxy or $N(CH_3)_2$, $R^3$ is $(C_1-C_4)$-alkyl, halogen, nitro or $(C_1-C_4)$-alkoxy, n is 0 or 1.

9. A compound or a salt thereof, as claimed in claim 8, wherein $R^3$ is $(C_1-C_4)$-alkyl, halogen, nitro or $(C_1-C_4)$-alkoxy, $R^4$ is H, A is a radical of the formula

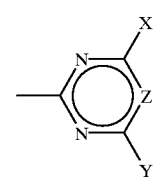

X is $(C_1-C_2)$-alkyl or $(C_1-C_2)$-alkoxy,

Y is $(C_1-C_2)$-alkyl or $(C_1-C_2)$-alkoxy, m is 0, and n is 0.

10. A compound or a salt thereof, as claimed in claim 9, wherein $R^2$ is H,

X is methyl or methoxy, and

Y is methyl or methoxy.

11. A Compound of the formula (I) or a salt thereof,

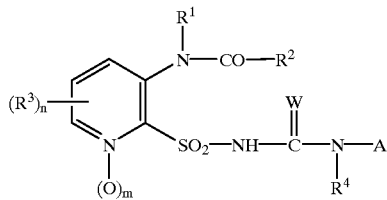

(I)

in which $R^1$ is H, $(C_1-C_6)$alkyl which is unsubstituted or substituted by one or more radicals selected from the group consisting of halogen, nitro, $(C_1-C_6)$alkoxy, aryl and substituted aryl, or aryl in which the aryl radical is unsubstituted or substituted by one or more radicals selected from the group consisting of halogen, nitro, $(C_1-C_4)$alkyl, $(C_1-C_4)$haloalkyl and $(C_1-C_4)$alkoxy, $R^2$ is H, $(C_1-C_6)$alkyl, $(C_2-C_6)$alkenyl or $(C_2-C_6)$-alkynyl, each of the three last-mentioned radicals being unsubstituted or substituted by one or more radicals selected from the group consisting of halogen, $(C_1-C_4)$alkoxy, $(C_1-C_4)$alkylthio, $(C_1-C_4)$alkylsulfynyl, $(C_1-C_4)$alkylsulfonyl, nitro, cyano and thiocyanato, or is $(C_3-C_7)$-cycloalkyl which is unsubstituted or substituted by one or more radicals selected from the group consisting or $(C_1-C_4)$alkyl, $(C_1-C_4)$alkoxy, $(C_1-C_4)$alkylthio, $(C_1-C_4)$haloalkyl and halogen, or aryl, substituted aryl, or a radical of the formula $NR^aR^b$, $R^3$ is $(C_1-C_4)$alkyl, $(C_1-C_3)$haloalkyl, halogen, $NO_2$, CN, $(C_1-C_4)$alkoxy, $(C_1-C_3)$haloalkoxy, $(C_1-C_3)$-alkylthio, $(C_1-C_3)$alkoxy-$(C_1-C_3)$alkyl, $[(C_1-C_3)$-alkoxy]-carbonyl, $(C_1-C_3)$alkylamino, $di[(C_1-C_3)$-alkyl]-amino, $(C_1-C_6)$-alkylsulfynyl, $(C_1-C_3)$-alkylsuflonyl, $SO_2NR^cR^d$ or $C(O)NR^eR^f$, $R^a, R^b, R^c, R^d, R^e$ and $R^f$ independently of one another are H, $(C_1-C_4)$alkyl, $(C_3-C_6)$alkenyl, $(C_3-C_6)$-alkynyl, $[(C_1-C_4)$alkyl]-carbonyl, arylcarbonyl, which is unsubstituted or substituted in the aryl radical, or the pairs $R^a$ and $R^b$, $R^c$ and $R^d$ or $R^e$ and $R^f$ together with the N atom linking them are a heterocyclic saturated or unsaturated ring selected from the group consisting of pyrrole, imidazole, pyrazole, triazole, pyrrazolone, oxazole, oxazolene, propane sultams, butane sultams, pyrrolidone, piperidine and morpholine, $R^4$ is H or $(C_1-C_4)$alkyl, m is 0 or 1, n in 0, 1 or 2, A is a radical of the formula

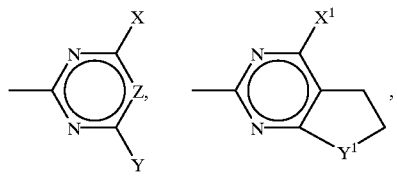

-continued

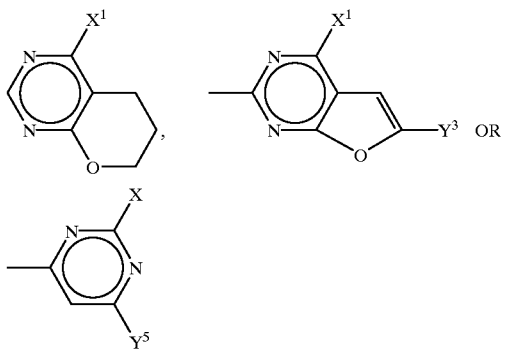

X and Y independently of one another are H, halogen, $(C_1-C_3)$alkyl, $(C_1-C_3)$alkoxy or $(C_1-C_3)$alkylthio, the abovementioned alkyl-containing radicals being unsubstituted or mono- or polysubstituted by halogen or mono-disubstituted by $(C_1-C_3)$-alkoxy or $(C_1-C_3)$ alkylthio, or a radical of the formula $NR^5R^6$, $(C_3-C_6)$ cycloalkyl, $(C_2-C_4)$alkenyl, $(C_2-C_4)$alkynyl, $(C_3-C_4)$ alkenyloxy or $(C_3-C_4)$-alkynyloxy, $R^5$ and $R^6$ independently of one another are H, $(C_1-C_3)$ alkyl or $(C_3-C_4)$alkenyl, W is O or S, Z is CH, $X^1$ is $CH_3$, $OCH_3$, $OC_2H_5$ or $OCF_2H$, $Y^1$ is —O— or —$CH_2$—, $Y^3$ is H or $CH_3$, $Y^5$ is $CH_3$, $C_2H_5$, or Cl.

12. A compound or a salt thereof, as claimed in claim 11, wherein $R^1$ is H, $(C_1-C_6)$alkyl which is unsubstituted or substituted by 1 to 3 radicals selected from the group consisting of halogen or by $(C_1-C_2)$alkoxy.

13. A compound or a salt thereof, as claimed in claim 11, wherein $R^2$ is H, $(C_1-C_4)$alkyl which is unsubstituted or substituted by one or more halogen atoms or by $(C_1-C_2)$ alkoxy, or $(C_2-C_4)$alkenyl, $(C_2-C_4)$alkynyl, $(C_3-C_5)$ cycloalkyl or a radical of the formula $NR^aR^b$ in which $R^a$ and $R^b$ independently of one another are H or $(C_1-C_4)$alkyl.

14. A compound or a salt thereof, as claimed in claim 11, wherein $R^3$ is $(C_1-C_4)$alkyl, $(C_1-C_3)$haloalkyl, halogen, $(C_1-C_3)$ alkoxy or nitro and n is 0, 1 or 2.

15. A compound or a salt thereof, as claimed in claim 11, wherein

A is a radical of the formula

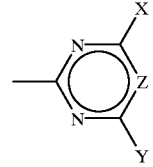

in which one of the radicals X and Y is $(C_1-C_3)$-alkyl, $(C_1-C_3)$alkoxy, $(C_1-C_3)$haloalkyl, $(C_1-C_3)$-haloalkoxy or $[(C_1-C_2)$alkoxy]-$(C_1-C_2)$alkyl and the other radical Y or X is $(C_1-C_3)$alkyl, $(C_1-C_3)$alkoxy or $(C_1-C_3)$alkylthio, where each of the last-mentioned 3 radicals is unsubstituted or mono- or polysubstituted by halogen or mono- or disubstituted by $(C_1-C_3)$alkoxy or $(C_1-C_3)$-alkylthio, or halogen, or a radical of the formula $NR^5R^6$ in which $R^5$ and $R^6$ independently of one another are H, $(C_1-C_3)$alkyl or $(C_3-C_4)$-alkenyl, or $(C_3-C_5)$cycloalkyl, $(C_2-C_4)$alkenyl, $(C_2-C_4)$alkynyl, $(C_3-C_4)$alkenyloxy or $(C_3-C_4)$-alkynyloxy.

16. A compound or a salt thereof, as claimed in claim 11, wherein $R^1$ is H, $(C_1-C_4)$alkyl, $(C_1-C_4)$haloalkyl or $[(C_1-C_2)$-alkoxy$]$-$(C_1-C_2)$alkyl, $R^2$ is H, $(C_1-C_4)$alkyl, halo-$(C_1-C_4)$alkyl, $(C_2-C_4)$alkenyl, $(C_2-C_4)$alkynyl, $[(C_1-C_2)$alkoxy$]$-$(C_1-C_2)$alkyl, $(C_3-C_5)$cycloalkyl or a radical of the formula $NR^aR^b$ in which $R^a$ and $R^b$ independently of one another are H or $(C_1C_4)$alkyl, $R^3$ is $(C_1-C_4)$alkyl, halogen, nitro or $(C_1-C_4)$alkoxy and n is 0 or 1.

17. A compound or a salt thereof, as claimed in claim 11, wherein one of the radicals X or Y is $(C_1-C_2)$alkyl, $(C_1-C_2)$alkoxy or $OCF_2H$ and the other radical Y or X is $(C_1-C_2)$alkyl, $(C_1-C_2)$alkoxy, halogen, $OCF_2H$, $OCH_2CF_3$ or $CF_3$.

18. A compound or a salt thereof, as claimed in claim 12, wherein $R^2$ is H, $(C_1-C_4)$alkyl which is unsubstituted or substituted by one or more halogen atoms or by $(C_1-C_2)$alkoxy, or $(C_2-C_4)$alkenyl, $(C_2-C_4)$alkynyl, $(C_3-C_5)$cycloalkyl or a radical of the formula $NR^aR^b$ in which $R^a$ and $R^b$ independently of one another are H or $(C_1-C_4)$alkyl.

19. A compound or a salt thereof, as claimed in claim 18, wherein $R^3$ is $(C_1-C_4)$alkyl, $(C_1-C_3)$haloalkyl, halogen, $(C_1-C_3)$alkoxy or nitro and n is 0, 1 or 2.

20. A compound or a salt thereof, as claimed in claim 19, wherein

A is a radical of the formula

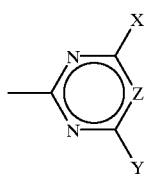

in which one of the radicals X and Y is $(C_1-C_3)$-alkyl, $(C_1-C_3)$alkoxy, $(C_1-C_3)$haloalkyl, $(C_1-C_3)$-haloalkoxy or $[(C_1-C_2)$alkoxy$]$-$(C_1-C_2)$alkyl and the other radical Y or X is $(C_1-C_3)$alkyl, $(C_1-C_3)$alkoxy or $(C_1-C_3)$alkylthio, where each or the last-mentioned 3 radicals is unsubstituted or mono- or polysubstituted by halogen or mono- or disubstituted by $(C_1-C_3)$alkoxy or $(C_1-C_3)$-alkylthio, or halogen, or a radical of the formula $NR^5R^6$ in which $R^5$ and $R^6$ independently of one another are H, $(C_1-C_3)$alkyl or $(C_3-C_4)$-alkenyl, or $(C_3-C_5)$cycloalkyl, $(C_2-C_4)$alkenyl, $(C_2-C_4)$alkynyl, $(C_3-C_4)$alkenyloxy or $(C_3-C_4)$-alkynyloxy.

21. A compound or a salt thereof, as claimed in claim 20, wherein $R^1$ is H, $(C_1-C_4)$alkyl, $(C_1-C_4)$haloalkyl or $[(C_1-C_2)$-alkoxy$]$-$(C_1-C_2)$alkyl, $R^2$ is H, $(C_1-C_4)$alkyl, halo-$(C_1-C_4)$alkyl, $(C_2-C_4)$alkenyl, $(C_2-C_4)$alkynyl, $[(C_1-C_2)$alkoxy$]$-$(C_1-C_2)$alkyl, $(C_3-C_5)$cycloalkyl or a radical of the formula $NR^aR^b$ in which $R^a$ and $R^b$ independently of one another are H or $(C_1-C_4)$alkyl, $R^3$ is $(C_1-C_4)$alkyl, halogen, nitro or $(C_1-C_4)$alkoxy and n is 0 or 1.

22. A compound or a salt thereof, as claimed in claim 21, wherein one of the radicals X or Y is $(C_1-C_2)$alkyl, $(C_1-C_2)$alkoxy or $OCF_2H$ and the other radical Y or X is $(C_1-C_2)$alkyl, $(C_1-C_2)$alkoxy, halogen, $OCF_2H$, $OCH_2CF_3$ or $CF_3$.

23. A Compound of the formula (I) or a salt thereof, as claimed in claim 11

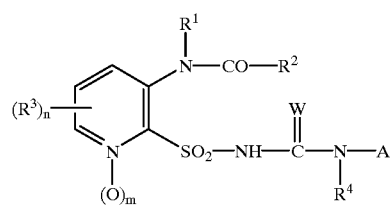

(I)

in which $R^1$ is H, $(C_1-C_6)$alkyl which is unsubstituted or substituted by one or more radicals selected from the group consisting of halogen, nitro, $(C_1-C_4)$alkoxy, aryl and substituted aryl, or aryl in which the aryl radical is unsubstituted or substituted by one or more radicals selected from the group consisting of halogen, nitro, $(C_1-C_4)$alkyl, $(C_1-C_4)$-haloalkyl and $(C_1-C_4)$alkoxy, $R^2$ is H, $(C_1-C_6)$alkyl, $(C_2-C_6)$alkenyl or $(C_2-C_6)$-alkynyl, each of the three last-mentioned radicals being unsubstituted or substituted by one or more radicals selected from the group consisting of halogen, $(C_1-C_4)$alkoxy, $(C_1-C_4)$alkylthio, $(C_1-C_4)$alkylsulfynyl, $(C_1-C_4)$alkylsulfonyl, nitro, cyano and thiocyanato, or is $(C_3-C_7)$-cycloalkyl which is unsubstituted or substituted by one or more radicals selected from the group consisting of $(C_1-C_4)$alkyl, $(C_1-C_4)$alkoxy, $(C_1-C_4)$alkylthio, $(C_1-C_4)$haloalkyl and halogen, or phenyl, phenyl substituted by one or more radicals selected from the group consisting of halogen, $(C_1-C_4)$alkyl, $(C_1-C_4)$haloalkyl, $(C_1-C_4)$haloalkyl, nitro, cyano, $(C_1-C_4)$alkoxycarbonyl, $(C_1-C_4)$alkanoyl, carbamoyl, mono- and di$(C_1-C_4)$alkylaminocarbonyl, mono- and di-$(C_1-C_4)$alkylamino, $(C_1-C_4)$alkylsulfinyl and $(C_1-C_4)$alkylsulfonyl or a radical of the formula $NR^aR^b$, $R^3$ is $(C_1-C_4)$alkyl, $(C_1-C_3)$haloalkyl, halogen, $NO_2$, CN, $(C_1-C_4)$alkoxy, $(C_1-C_3)$haloalkoxy, $(C_1-C_3)$-alkylthio, $(C_1-C_3)$alkoxy-$(C_1-C_3)$alkyl, $[(C_1-C_3)$-alkoxy$]$-carbonyl, $(C_1-C_3)$alkylamino, di$[(C_1-C_3)$-alkyl$]$-amino, $(C_1-C_6)$-alkylsulfynyl, $(C_1-C_3)$-alkylsuflonyl, $SO_2NR^cR^d$ or $C(O)NR^eR^f$, $R^a, R^b, R^c, R^d, R^e$ and $R^f$ independently of one another are H, $(C_1-C_4)$alkyl, $(C_3-C_6)$alkenyl, $(C_3-C_6)$alkynyl, $[(C_1-C_4)$alkyl$]$-carbonyl, arylcarbonyl, which is unsubstituted or substituted in the aryl radical, or the pairs $R^a$ and $R^b$, $R^c$ and $R^d$ or $R^e$ and $R^f$ together with the N atom linking then are a heterocyclic saturated or unsaturated ring selected from the group consisting of pyrrole, imidazole, pyrazole, triazole, pyrrazolone, oxazole, oxazolene, propane sultams, butane sultams, pyrrolidone, piperidine and morpholine, R⁴ is H or $(C_1-C_4)$alkyl,
m is 0 or 1,
n is 0, 1 or 2,
A is a radical of the formula

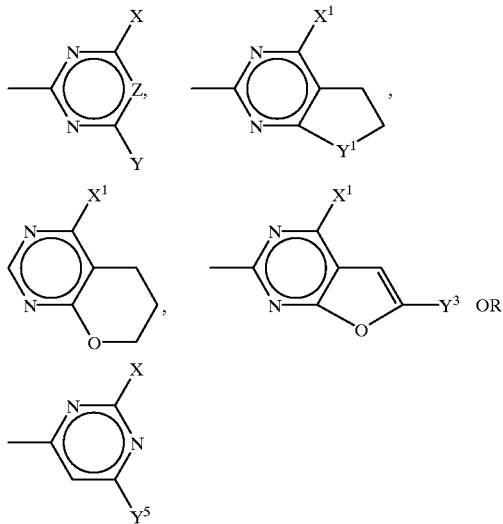

X and Y independently of one another are H, halogen, $(C_1-C_3)$alkyl, $(C_1-C_3)$alkoxy or $(C_1-C_3)$alkylthio, the abovementioned alkyl-containing radicals being unsubstituted or mono- or polysubstituted by halogen or mono-disubstituted by $(C_1-C_3)$-alkoxy or $(C_1-C_3)$ alkylthio, or a radical of the formula $NR^5R^6$, $(C_3-C_6)$ cycloalkyl, $(C_2-C_4)$alkenyl, $(C_2-C_4)$alkynyl, $(C_3-C_4)$ alkenyloxy or $(C_3-C_4)$alkynyloxy, $R^5$ and $R^6$ independently of one another are H, $(C_1-C_3)$ alkyl or $(C_3-C_4)$alkenyl, W is O or S,
Z is CH,
$X^1$ in $CH_3$, $OCH_3$, $OC_2H_5$ or $OCF_2H$,
$Y^1$ is —O— or —$CH_2$—,
$Y^3$ is R or $CH_3$,
$Y^5$ is $CH_3$, $C_2H_5$ or Cl.

24. A compound as claimed in claim 11, wherein $R^1$ is hydrogen, $R^2$ is ethyl, n is zero, X is methoxy, Y is methoxy and Z is CH.

25. A compound as claimed in claim 11, wherein $R^1$ is hydrogen, $R^2$ is hydrogen, n is zero, X is methoxy, Y is methoxy and Z is CH.

26. A compound as claimed in claim 11, wherein $R^1$ is hydrogen, $R^2$ is hydrogen, n is zero, X is ethoxy, y is ethoxy and Z is CH.

27. A compound as claimed in claim 11, wherein $R^1$ is hydrogen, $R^2$ is isopropyl, n is zero, X is methoxy, Y is methoxy and Z in CH.

28. A compound as claimed in claim 11, wherein $R^1$ is hydrogen, $R^2$ is $CF_3$, n is zero, X is methoxy, Y is methoxy and Z is CH.

29. A compound as claimed in claim 11, wherein $R^1$ is hydrogen, $R^2$ is cyclopropyl, n is zero, X is methoxy, Y is methoxy and Z is CH.

30. A compound as claimed in claim 11, wherein $R^1$ is hydrogen, $R^2$ is methyl, n is zero, X is methyl, Y is methyl and Z is CH.

31. A compound as claimed in claim 11, wherein $R^1$ is hydrogen, $R^2$ is dimethylamino, n is zero, X is methoxy, Y is methoxy and Z is CH.

32. A compound as claimed in claim 11, wherein $R^1$ is hydrogen, $R^2$ is phenyl, n is zero, X is methoxy, Y is methoxy and Z is CH.

33. A compound as claimed in claim 11, wherein $R^1$ is hydrogen, $R^2$ is ethenyl, n is zero, X is methoxy, Y is methoxy and Z is CH.

34. A compound as claimed in claim 11, wherein $R^1$ is hydrogen, $R^2$ cyclobutyl, n is zero, X is methoxy, Y is methoxy and Z is CH.

35. A compound as claimed in claim 11, wherein $R^1$ is hydrogen, $R^2$ is methoxymethyl, n is zero, X is methoxy, Y in methoxy and Z is CH.

36. A compound as claimed in claim 11, wherein $R^1$ is methyl, $R^2$ is methyl, n is zero, X is methoxy, Y is methoxy and Z is CH.

37. A compound as claimed in claim 11, wherein $R^1$ is methyl, $R^2$ is methyl, n is zero, X is methoxy, Y is methoxy and Z is CH.

38. A compound as claimed in claim 11, wherein $R^1$ is methyl, $R^2$ is $CF_3$, h is zero, X is methoxy, Y is methoxy and Z is CH.

39. A compound as claimed in claim 11, wherein $R^1$ is methyl, $R^2$ is isopropyl, n is zero, X is methoxy, Y is methoxy and Z is CH.

40. A compound as claimed in claim 11, wherein $R^1$ is methyl, $R^2$ is methyl, n is zero, X is methoxy, Y is methoxy and Z is CH.

41. A compound as claimed in claim 11, wherein $R^1$ is ethyl, $R^2$ in hydrogen, n is zero, X is methoxy, Y is methoxy and Z is CH.

42. A compound of the formula 1b

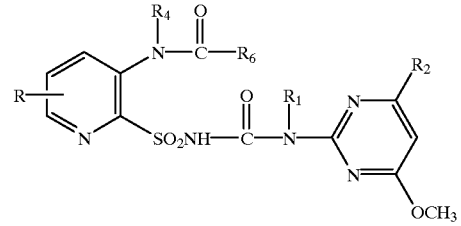

wherein hydrogen, halogen, $C_1-C_4$alkyl, $C_1-C_4$alkoxy or $C_1-C_4$alkylthio, or is $C_1-C_4$alkyl mono- or poly-substituted by halogen, $R_1$ is hydrogen or methyl; $R_2$ is methyl or methoxy; $R_4$ is hydrogen, $C_1-C_6$alkyl, or $C_1-C_6$alkyl that is mono- or polysubstituted by halogen, $C_1-C_6$alkoxy, $C_3-C_6$alkenyloxy, $C_3-C_6$alkynyloxy or by $C_1-C_6$alkylthio; $R_6$ is hydrogen, $C_1-C_6$alkyl, $C_3-C_6$cycloalkyl or $C_2-C_6$alkynyl; or is $C_1-C_6$alkyl or $C_3-C_6$cycloalkyl each substituted by halogen or by $C_1-C_4$alkoxy; or is $C_2-C_6$alkenyl, or $C_2-C_6$ substituted by halogen; or is phenyl, benzyl, naphthyl or $OR_{12}$, or phenyl, benzyl or naphthyl each substituted by halogen, $C_1-C_4$alkyl, $C_1-C_4$haloalkyl, $C_1-C_4$alkoxy, $C_1-C_4$haloalkoxy, $C_3-C_6$alkenyloxy, $C_3-C_6$alkynyloxy, nitro, cyano, $COOR_{13}$, $NR_{15}R_{16}$, $C(O)NR_{17}R_{18}$, $X_1R_{20}$, $SO_2NR_{21}R_{22}$ or by $X_2R_{23}$; $R_{12}$ is $C_1-C_6$alkyl, $C_1-C_6$haloalkyl, oxetan-3-yl, or $C_4-C_6$cycloalkyl, which may for its part be substituted by halogen, $C_1-C_4$alkyl or by $C_1-C_4$alkoxy; or is phenyl, benzyl or naphthyl, or phenyl, benzyl or naphthyl each substituted by $C_1-C_{alkyl}$, $C_1-C_4$haloalkyl, $C_1-C_4$alkoxy, $C_1-C_4$haloalkoxy, $C_1-C_4$alkylthio, $C_1-C_4$haloalkylthio, $C_1-C_4$alkylsulfonyl, $C_1-C_4$alkylsulfinyl, nitro, cyano, $COOR_{27}$, $NR_{25}R_{26}$, $CONR_{28}R_{29}$ or by $SO_2NR_{30}R_{14}$; or is $C_1-C_6$alkyl substituted by $C_1-C_4$alkoxy, $C_3-C_6$cycloalkyl, cyano, $COOR_{24}$ or by $CONR_{32}R_{33}$; or is $C_3-C_6$alkenyl, $C_3$–$C_6$haloalkenyl, $C_3$–$C_6$alkynyl, $C_3$–$C_6$haloalkynyl, $X_3N_{35}$ or $X_4R_{36}$; $R_{13}$ is hydrogen, $C_1$–$C_6$alkyl, $C_3$–$C_6$alkenyl, $C_3$–$C_6$alkynyl or oxetan-3-yl; $R_{14}$, $R_{15}$, $R_{16}$, $R_{17}$, $R_{18}$, $R_{21}$, $R_{22}$, $R_{25}$, $R_{26}$, $R_{28}$, $R_{29}$, $R_{30}$, $R_{32}$ and $R_{33}$ are each independently of the others hydrogen, $C_1$–$C_4$alkyl, $C_3$–$C_6$alkenyl or $C_3$–$C_6$alkynyl; or $R_{15}$ or $R_{25}$ are each independently of the other the groups —C(O)—$X_5$— $C_1$–$C_4$alkyl or —C(O)—$C_1$–$C_4$alkyl, which may for their part be substituted by halogen; or $R_{15}$ and $R_{16}$ or $R_{17}$ and $R_{18}$ or $R_{21}$ and $R_{22}$ or $R_{25}$ and $R_{26}$ or $R_{28}$ and $R_{29}$ or $R_{30}$ and $R_{14}$ or $R_{32}$ and $R_{33}$ together form a $C_4$–$C_5$alkylene chain, which may for its part be interrupted by oxygen or by $NR_{19}$, $R_{19}$ is hydrogen, $C_1$–$C_4$alkyl, $C_3$–$C_6$alkenyl or $C_3$–$C_6$alkynyl; $R_{20}$ and $R_{35}$ are each independently of the other $C_1$–$C_4$alkyl or $C_1$–$C_4$ haloalkyl; $R_{23}$ and $R_{36}$ are each independently of the other $C_1$–$C_4$alkyl substituted by $COOR_{34}$; $R_{24}$, $R_{27}$ and $R_{34}$ are each independently of the other hydrogen or $C_1$–$C_4$alkyl; $X_1$ and $X_3$ are each independently of the other sulfur, SO or $SO_2$; $X_2$ and $X_4$ are each independently of the other oxygen or sulfur; $X_5$ is oxygen or $NR_{37}$; and $R_{37}$ is hydrogen, $C_1$–$C_4$alkyl, $C_3$–$C_6$alkenyl or $C_3$–$C_6$alkynyl; or a compound of the formula (I) or a salt thereof,

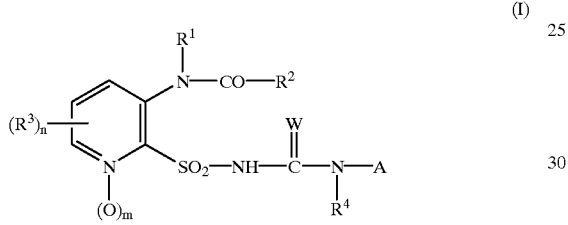

(I)

in which

- $R^1$ is H, ($C_1$–$C_6$)alkyl which in unsubstituted or substituted by one or more radicals selected from the group consisting of halogen, nitro, ($C_1$–$C_4$)alkoxy, aryl and substituted aryl, or aryl in which the aryl radical is unsubstituted or substituted by one or more radicals selected from the group consisting of halogen, nitro, ($C_1$–$C_4$)alkyl, ($C_1$–$C_4$)haloalkyl and ($C_1$–$C_4$)alkoxy,
- $R^2$ is H, ($C_1$–$C_6$)alkyl, ($C_2$–$C_6$)alkenyl or ($C_2$–$C_6$)alkynyl, each of the three last-mentioned radicals being unsubstituted or substituted by one or more radicals selected from the group consisting of halogen, ($C_1$–$C_4$)alkoxy, ($C_1$–$C_4$)alkylthio, ($C_1$–$C_4$)alkylsulfynyl, ($C_1$–$C_4$)alkylsulfonyl, nitro, cyano and thiocyanato, or is ($C_3$–$C_7$)-cycloalkyl which is unsubstituted or substituted by one or more radicals selected from the group consisting of ($C_1$–$C_4$)alkyl, ($C_1$–$C_4$)alkoxy, ($C_1$–$C_4$)alkylthio, ($C_1$–$C_4$)haloalkyl and halogen, or aryl, substituted aryl, or a radical of the formula $NR^aR^b$,
- $R^3$ is ($C_1$–$C_4$)alkyl, ($C_1$–$C_3$)haloalkyl, halogen, $NO_2$, CN, ($C_1$–$C_4$)alkoxy, ($C_1$–$C_3$)haloalkoxy, ($C_1$–$C_3$)-alkylthio, ($C_1$–$C_3$)alkoxy-($C_1$–$C_3$)alkyl, [($C_1$–$C_3$)-alkoxy]-carbonyl, ($C_1$–$C_3$)alkylamino, di[($C_1$–$C_3$)-alkyl]-amino, ($C_1$–$C_6$)-alkylsulfynyl, ($C_1$–$C_3$)-alkylsuflonyl, $SO_2NR^cR^d$ or $C(O)NR^eR^f$,
- $R^a$, $R^b$, $R^c$, $R^d$, $R^e$ and $R^f$ independently of one another are H, ($C_1$–$C_4$)alkyl, ($C_3$–$C_6$)alkenyl, ($C_3$–$C_6$)-alkynyl, [($C_1$–$C_4$)alkyl]-carbonyl, arylcarbonyl, which is unsubstituted or substituted in the aryl radical, or the pairs $R^a$ and $R^b$, $R^c$ and $R^d$ or $R^e$ and $R^f$ together with the N atom linking them are a heterocyclic saturated or unsaturated ring selected from th group consisting of pyrrole, imidazole, pyrazole, triazole, pyrrazolone, oxazole, oxazolene, propane sultams, butane sultams, pyrrolidone, piperidine and morpholine,
- $R^4$ is H or ($C_1$–$C_4$)alkyl,
- m 0 or 1,
- n is 0, 1 or 2,
- A is a radical of the formula

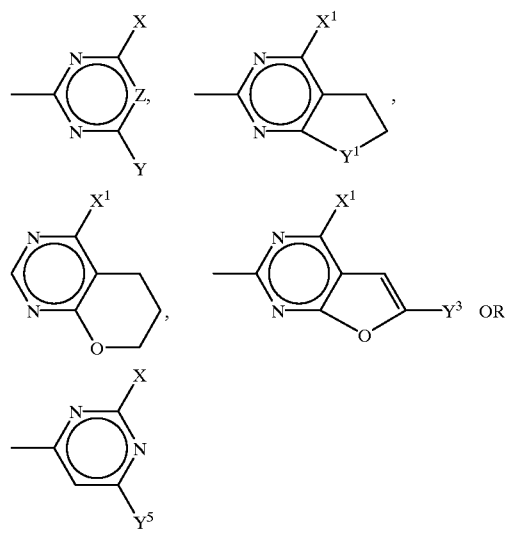

X and Y independently of one another are H, halogen, ($C_1$–$C_3$)alkyl, ($C_1$–$C_3$)alkoxy or ($C_1$–$C_3$)alkylthio, the abovementioned alkyl-containing radicals being unsubstituted or mono- or polysubstituted by halogen or mono- disubstituted by ($C_1$–$C_3$)-alkoxy or ($C_1$–$C_3$) alkylthio, or a radical of the formula $NR^5R^6$, ($C_3$–$C_6$) cycloalkyl, ($C_2$–$C_4$)alkenyl, ($C_2$–$C_4$)alkynyl, ($C_3$–$C_4$) alkenyloxy or ($C_3$–$C_4$)alkynyloxy, $R^5$ and $R^6$ independently of one another are H, ($C_1$–$C_3$) alkyl or ($C_3$–$C_4$)alkenyl, W is O or S, Z is CH, $X^1$ is $CH_3$, $OC_3$, $OC_2H_5$; or $OCF_2H$, $Y^1$ in —O— or —$CH_2$—, $Y^3$ is H or $CH_3$, $Y^5$ is $CH_3$, $C_2H_5$ or Cl.

43. A compound of the formula 1b

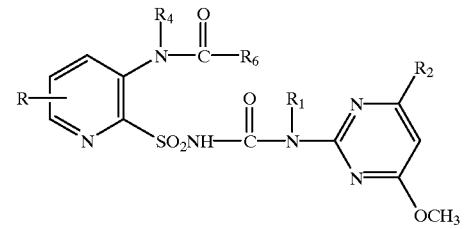

wherein R is hydrogen, halogen, $C_1$–$C_4$alkyl, $C_1$–$C_4$alkoxy or $C_1$–$C_4$alkylthio, or is $C_1$–$C_4$alkyl mono- or polysubstituted by halogen; $R_1$ is hydrogen or methyl; $R_2$ is methyl or methoxy; $R_4$ is hydrogen, $C_1$–$C_6$alkyl, or $C_1$–$C_6$alkyl that is mono- or polysubstituted by halogen, $C_1$–$C_6$alkoxy, $C_3$–$C_6$alkenyloxy, $C_3$–$C_6$alkynyloxy or by $C_1$–$C_6$alkylthio; $R_6$ is hydrogen, $C_1$–$C_6$alkyl, $C_3$–$C_6$cycloalkyl or $C_2$–$C_6$alkynyl; or is $C_1$–$C_6$alkyl or $C_3$–$C_6$cycloalkyl each substituted by halogen or by $C_1$–$C_6$alkoxy; or is $C_2$–$C_6$alkenyl, or $C_2$–$C_6$ substituted by halogen; or is phenyl, benzyl, naphthyl or $OR_{12}$, or phenyl, benzyl or naphthyl each substituted by halogen, $C_1$–$C_4$alkyl, $C_1$–$C_4$haloalkyl, $C_1$–$C_4$alkoxy, $C_1$–$C_4$haloalkoxy, $C_3$–$C_6$alkenyloxy, $C_3$–$C_6$alkynyloxy, nitro, cyano, $COOR_{13}$, $NR_{15}R_{16}$, $C(O)NR_{17}R_{18}$, $SO_2N_{21}R_{22}$ or by $X_2R_{23}$; $R_{12}$ is $C_1$–$C_6$alkyl, $C_1$–$C_6$haloalkyl, oxetan-3-yl, or $C_4$–$C_6$cycloalkyl, which may for its part be substituted by halogen, $C_1$–$C_4$alkyl or by $C_1$–$C_4$alkoxy; or is phenyl, benzyl or naphthyl, or phenyl, benzyl or naphthyl each substituted by $C_1$–$C_{alkyl}$, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfonyl, $C_1$–$C_4$alkylsulfinyl, nitro, cyano, $COOR_{27}$, $NR_{25}R_{26}$, $CONR_{28}R_{29}$, or by $SO_2NR_{30}R_{14}$; or is $C_1$–$C_6$alkyl substituted by $C_1$–$C_4$alkoxy, $C_3$–$C_6$cycloalkyl, cyano, $COOR_{24}$ or by $CONR_{32}R_{33}$; or is $C_3$–$C_6$alkenyl, $C_3$–$C_6$haloalkenyl, $C_3$–$C_6$alkynyl, $C_3$–$C_6$haloalkynyl, $X_3R_{35}$ or $X_4R_{36}$; $R_{13}$ is hydrogen, $C_1$–$C_6$alkyl, $C_3$–$C_6$alkenyl, $C_3$–$C_6$ alkynyl or oxetan-3-yl; $R_{14}$, $R_{15}$, $R_{16}$, $R_{17}$, $R_{18}$, $R_{21}$, $R_{22}$, $R_{25}$, $R_{26}$, $R_{28}$, $R_{29}$, $R_{30}$, $R_{32}$ and $R_{33}$ are each independently of the others hydrogen, $C_1$–$C_4$alkyl, $C_3$–$C_6$alkenyl or $C_3$–$C_6$alkynyl; or $R_{15}$ and $R_{25}$ are each independently of the other the groups —C(O)—$X_5$—$C_1$–$C_4$alkyl or —C(O)—$C_1$–$C_4$alkyl, which may for their part be substituted by halogen; or $R_{15}$ and $R_{16}$ or $R_{17}$ and $R_{18}$ or $R_{21}$ and $R_{22}$ or $R_{25}$ and $R_{26}$ or $R_{28}$ and $R_{29}$ or $R_{30}$ and $R_{14}$ or $R_{32}$ and $R_{33}$ together form a $C_4$–$C_5$alkylene chain, which may for its part be interrupted by oxygen or by $NR_{19}$, $R_{19}$ is hydrogen, $C_1$–$C_4$alkyl, $C_3$–$C_6$alkenyl or $C_3$–$C_6$alkynyl; $R_{20}$ and $R_{35}$ are each independently of the other $C_1$–$C_4$alkyl or $C_1$–$C_4$haloalkyl; $R_{23}$ and $R_{36}$ are each independently of the other $C_1$–$C_4$alkyl substituted by COOR34; $R_{24}$, $R_{27}$ and $R_{36}$ are each independently of the other hydrogen or $C_1$–$C_4$alkyl; $X_1$ and $X_3$ are each independently of the other sulfur, SO or $SO_2$; $X_2$ and $X_4$ are each independently of the other oxygen or sulfur; $X_5$ is oxygen or $NR_{37}$; and $R_{37}$ is hydrogen, $C_1$–$C_4$alkyl, $C_3$–$C_6$alkenyl or $C_3$–$C_6$alkynyl; or a compound of the formula (I) or a salt thereof,

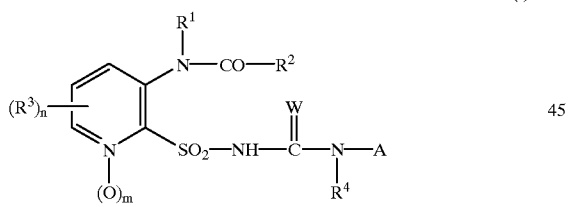

(I)

in which $R^1$ is H, ($C_1$–$C_6$)alkyl which is unsubstituted or substituted by one or more radicals selected from the group consisting of halogen, nitro, ($C_1$–$C_4$)alkoxy, ($C_3$–$C_6$) cycloalkyl, aryl and substituted aryl, or aryl in which the aryl radical is unsubstituted or substituted by one or more radicals selected from the group consisting of halogen, nitro, ($C_1$–$C_4$)alkyl, ($C_1$–$C_4$)-haloalkyl and ($C_1$–$C_4$)alkoxy, $R^2$ is H, ($C_1$–$C_6$)alkyl, ($C_2$–$C_6$)alkenyl or ($C_2$–$C_6$)alkynyl, each of the three last-mentioned radicals being unsubstituted or substituted by one or more radicals selected from the group consisting of halogen, ($C_1$–$C_4$)alkoxy, ($C_1$–$C_4$)alkylthio, ($C_1$–$C_4$)alkylsulfynyl, ($C_1$–$C_4$) alkylsulfonyl, nitro, cyano and thiocyanato, or ($C_1$–$C_6$) alkoxy or ($C_1$–$C_6$)alkylthio, the last-mentioned 2 radicals being unsubstituted or substituted by one or more radicals selected from the group consisting of halogen, ($C_1$–$C_4$)alkoxy, ($C_1$–$C_4$)alkylthio, aryl and substituted aryl, ($C_3$–$C_7$) -cycloalkyl or ($C_3$–$C_7$)cycloalkoxy, the last-mentioned 2 radicals being unsubstituted or substituted by one or more radicals selected from the group consisting of ($C_1$–$C_4$)alkyl, ($C_1$–$C_4$)alkoxy, ($C_1$–$C_4$) alkylthio, ($C_1$–$C_4$)haloalkyl and halogen, or aryl, substituted aryl, or a radical of the formula $NR^aR^b$, $R^3$ is ($C_1$–$C_4$)alkyl, ($C_1$–$C_3$)haloalkyl, halogen, $NO_2$, CN, ($C_1$–$C_3$)alkoxy, ($C_1$–$C_3$)haloalkoxy, ($C_1$–$C_3$)-alkylthio, ($C_1$–$C_3$)alkoxy-($C_1$–$C_3$)alkyl, [($C_1$–$C_3$)-alkoxy]-carbonyl, ($C_1$–$C_3$)alkylamino, di[($C_1$–$C_3$)-alkyl]-amino, ($C_1$–$C_6$)-alkylsulfynyl, ($C_1$–$C_3$)-alkylsuflonyl, $SO_2NR^cR^d$ or $C(O)NR^eR^f$, $R^a$, $R^b$, $R^c$, $R^d$, $R^e$ and $R^f$ independently of one another are H, ($C_1$–$C_4$)alkyl, ($C_3$–$C_6$)alkenyl, ($C_3$–$C_6$)-alkynyl, [($C_1$–$C_4$)alkyl]-carbonyl, arylcarbonyl, which is unsubstituted or substituted in the aryl radical, or the pairs $R^a$ and $R^b$, $R^c$ and $R^d$ or $R^e$ and $R^f$ together with the N atom linking them are a heterocyclic saturated or unsaturated ring selected from the group consisting of pyrrole, imidazole, pyrazole, triazole, pyrrazolone, oxazole, oxazolene, propane sultams, butane sultams, pyrrolidone, piperidine and morpholine, $R^4$ is H or ($C_1$–$C_4$)alkyl, m is 0 or 1, n is 0, 1 or 2, A is a radical of the formula

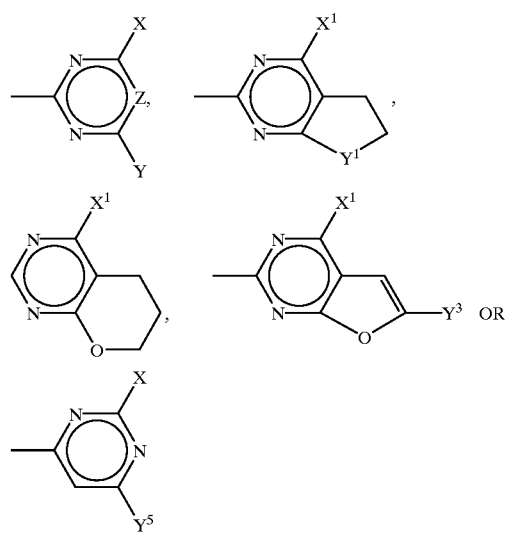

X and Y independently of one another are H, halogen, ($C_1$–$C_3$)alkyl, ($C_1$–$C_3$)alkoxy or ($C_1$–$C_3$)alkylthio, the abovementioned alkyl-containing radicals being unsubstituted or mono- or polysubstituted by halogen or mono- disubstituted by ($C_1$–$C_3$)-alkoxy or ($C_1$–$C_3$) alkylthio, or a radical of the formula $NR^5R^6$, ($C_3$–$C_6$) cycloalkyl, ($C_2$–$C_4$)alkenyl, ($C_2$–$C_4$)alkynyl, ($C_3$–$C_4$) alkenyloxy or ($C_3$–$C_4$)alkynyloxy, $R^5$ and $R^6$ independently of one another are H, ($C_1$–$C_3$) alkyl or ($C_3$–$C_4$)alkenyl, W is O or S, Z is CH, $X^1$ is $C_3$, $OCH_3$, $OC_2H_5$ or $OCF_2H$, $Y^1$ is —O— or —$CH_2$—, Y³ is H or CH₃,
Y⁵ is CH₃, C₂R₅ or Cl.

44. A Compound of the formula (I) or a salt thereof as claimed in claim 14, wherein R³ is (C₁–C₄)alkyl, (C₁–C₃)haloalkyl, halogen, NO₂, CN, (C₁–C₃)alkoxy, (C₁–C₃)haloalkoxy, (C₁–C₃)-alkylthio, (C₁–C₃)alkoxy-(C₁–C₃)alkyl, [(C₁–C₃)-alkoxy]-carbonyl, (C₁–C₃)alkylamino, di[(C₁–C₃)-alkyl]-amino, (C₁–C₆)-alkylsulfynyl, (C₁–C₃)-alkylsuflonyl, SO₂NR$^c$R$^d$ or C(O)NR$^e$R$^f$.

45. A process for the preparation of a compound or a salt thereof as claimed in any one of claims 1, 11, 42 or 43, which comprises a) reacting a compound of the formula (II)

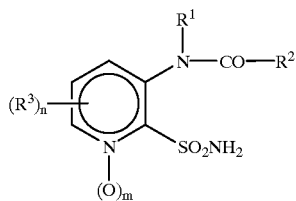
(II)

with a heterocyclic carbamate of the formula (III)

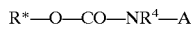

R*—O—CO—NR⁴—A          (III)

in which R* is optionally substituted phenyl or (C₁–C₄) alkyl, or b) reacting a pyridylsulfonylcarbamate of the formula (IV)

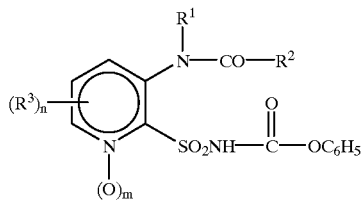
(IV)

with an amino heterocycle of the formula (V)

H—NR⁴—A          (V)

or c) reacting a sulfonyl isocyanate of the formula (VI)

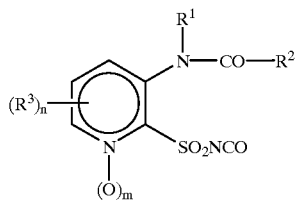
(VI)

with an amino heterocycle of the formula (V)

H—NR⁴—A          (V)

or d) reacting, in a one-pot reaction, first an amino heterocycle of the formula H—NR⁴—A (V) with phosgene in the presence of a base and reacting the intermediate formed with a pyridine-sulfonamide of the formula (II), where, in formulae (II)–(VI), R¹, R², R³, R⁴, A, m and n are as defined in formula I.

46. A process for the preparation of a compound of formula (II) in which R¹, R², R³, m and n are as defined in claim 1,

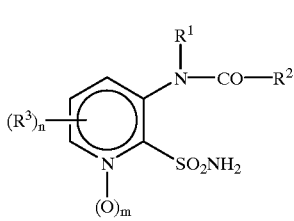
(II)

which comprises reacting a compound of the formula (VII)

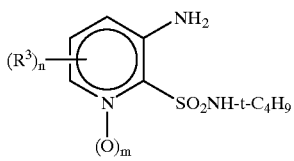
(VII)

in which R², m and n are as defined in formula (II), with carboxylic acid halides of the formula Hal—CO—R² (Hal= halogen) or symmetric or mixed carboxylic anhydrides of the formula R²—CO—O—CO—R⁺ in which R⁺ is defined analogously to R² or is another aliphatic or aromatic radical, and subsequently reacting the resulting 3-(N-acylamino)-pyridine2-sulfamide which is protected with the t-butyl group a) with a strong acid to give the free 3-(N-acylamino) pyridine-2-sulfamide of the formula (II) in which R¹=H, or b) reducing it to the N-alkyl compound, N-acylating the N-alkyl compound with a compound of the formula Hal—CO—R² or R²—CO—O—CO—R⁺ and eliminating the t-butyl protective group with a strong acid, giving the free 3-(N-acylamino)pyridine-2-sulfamide of the formula (II) in which R¹ is other than hydrogen.

* * * * *